United States Patent
Ray et al.

(10) Patent No.: US 10,188,726 B2
(45) Date of Patent: Jan. 29, 2019

(54) SYNTHETIC HEPATITIS C POLYPEPTIDE AND METHODS OF MAKING AND USING SAME

(71) Applicant: THE JOHNS HOPKINS UNIVERSITY, Baltimore, MD (US)

(72) Inventors: Stuart Campbell Ray, Lutherville, MD (US); Supriya Munshaw, Baltimore, MD (US); Lin Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/335,659

(22) Filed: Oct. 27, 2016

(65) Prior Publication Data

US 2017/0043011 A1    Feb. 16, 2017

Related U.S. Application Data

(62) Division of application No. 14/114,808, filed as application No. PCT/US2012/036098 on May 2, 2012, now Pat. No. 9,512,183.

(60) Provisional application No. 61/481,457, filed on May 2, 2011.

(51) Int. Cl.
| | |
|---|---|
| *A61K 39/29* | (2006.01) |
| *G01N 33/576* | (2006.01) |
| *C07K 16/10* | (2006.01) |
| *C12N 7/00* | (2006.01) |
| *G01N 33/569* | (2006.01) |
| *C07K 14/005* | (2006.01) |
| *C12N 9/02* | (2006.01) |
| *A61K 39/12* | (2006.01) |
| *A61K 39/00* | (2006.01) |

(52) U.S. Cl.
CPC .............. *A61K 39/29* (2013.01); *A61K 39/12* (2013.01); *C07K 14/005* (2013.01); *C07K 16/109* (2013.01); *C12N 7/00* (2013.01); *C12N 9/0069* (2013.01); *G01N 33/56983* (2013.01); *G01N 33/5767* (2013.01); *A61K 2039/53* (2013.01); *C12N 2770/24221* (2013.01); *C12N 2770/24234* (2013.01)

(58) Field of Classification Search
None
See application file for complete search history.

(56) References Cited

U.S. PATENT DOCUMENTS

| | | | |
|---|---|---|---|
| 6,027,729 | A | 2/2000 | Houghton et al. |
| 7,235,394 | B1 | 6/2007 | Rice et al. |
| 2009/0238822 | A1 | 9/2009 | George et al. |

FOREIGN PATENT DOCUMENTS

| | | |
|---|---|---|
| JP | 2001-515353 A | 9/2001 |
| JP | 2011-505867 A | 3/2011 |
| WO | 2010-039154 A1 | 4/2010 |
| WO | 2010-073204 A1 | 7/2010 |

OTHER PUBLICATIONS

Hsu et al. Proc Natl Acad Sci U S A. Jun. 10, 2003;100(12):7271-6. Epub May 21, 2003.*
Accession B3TKN6. Sep. 2, 2008 (alginment to Seq ID No. 1).*
Meunier, J., et al., (2008) "Isolation and characterization of broadly neutralizing human monoclonal antibodies to the e1 glycoprotein of hepatitis C virus" J.Virol., vol. 82, pp. 966-973.
Keck, Y., et al., (2004) "Human monoclonal antibody to hepatitis C virus E1 glycoprotein that blocks virus attachment and viral infectivity", J. Virol., vol. 78, pp. 7257-7263.
Synthetic construct Hepatitis C virus Bole1a, complete genome, GenBank [online], Accession No. JQ791196, Apr. 30, 2012 uploaded, [retrieved on Apr. 6, 2016], URL,http://www.ncbi.nlm.nih.gov/nuccore/JQ791196.
Hsu, M. et al., (2003) "Hepatitis C virus glycoproteins mediate pH-dependent cell entry of pseudotyped retroviral particles", Proc. Natl. Acad. Sci.U. S. A., vol. 100, pp. 7271-7276.
Supplementary European Search Report dated Oct. 8, 2014 for EP Application 12779797.5.
Office Action dated Apr. 12, 2016 for JP Application 2014-509382.
Grakoui, A., et al., (1993) "Expression and identification of hepatitis C virus polyprotein polyprotein cleavage products" J.Virol., vol. 67, No. 3, pp. 1385-1395.
GenBank Accession No. AF009606 (Jun. 18, 2009) "Hepatitis C virus subtype 1a polyprotein gene".
Chevaliez, S., et al., (2009) "Hepatitis C virus (HCV) genotype 1 subtype identification in new HCV drug development and future clinical practice" PLoS ONE, vol. 4, No. 12, e8209.

* cited by examiner

*Primary Examiner* — Christian L Fronda
(74) *Attorney, Agent, or Firm* — John Hopkins Technology Ventures

(57) ABSTRACT

Synthetic representative HCV subtypes, including a 1a and 1b genome, dubbed Bole1a and Bole1b, are provided using an inventive method of Bayesian phylogenetic tree analysis, ancestral sequence reconstruction and covariance analysis. Bole1a branches centrally among 390 full-genome sequences used in its design, a carefully curated 143 sequence full-genome dataset, and separate genomic regions including an independent set of 214 E1E2 sequences from a Baltimore cohort. Bole1a is phylogenetically representative of widely circulating strains. Full genome non-synonymous diversity comparison and 9-mer peptide coverage analysis showed that Bole1a is able to provide more coverage (94% and 78% respectively) than any other sequence in the dataset including H77, a traditional reference sequence. Bole1a also provides unsurpassed epitope coverage when compared to all known T cell epitopes.

4 Claims, 7 Drawing Sheets
Specification includes a Sequence Listing.

FIG. 2A

SEQUENCE LISTING

```
<160> NUMBER OF SEQ ID NOS: 8

<210> SEQ ID NO 1
<211> LENGTH: 9607
<212> TYPE: DNA
<213> ORGANISM: Artificial Sequence
<220> FEATURE:
<223> OTHER INFORMATION: synthetic sequence

<400> SEQUENCE: 1
gccagccccc tgatgggggc gacactccac catgaatcac tccctgtga ggaactactg      60 tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gataaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag gaagacttcc gagcggtcgc aacctcgagg tagacgtcag cctatcccca     540
aggcgcgtcg gcccgagggc aggacctggg ctcagcccgg gtaccttgg cccctctatg     600
```

```
gcaatgaggg ctgcgggtgg gcgggatggc tcctgtctcc ccgtggctct cggcctagct    660
ggggccccac agaccccgg cgtaggtcgc gcaatttggg taaggtcatc gatacccttta    720 cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaact cctcggggct ttaccatgtc accaatgatt    960
gccctaactc gagtattgtg tacgaggcgg ccgatgccat cctgcacact ccggggtgtg   1020
tcccttgcgt tcgcgagggt aacgcctcga ggtgttgggt ggcgttgacc ccacggtgg    1080 ccaccaggga cggcaaactc cccacaacgc agcttcgacg tcacatcgat ctgcttgtcg   1140
ggagcgccac cctctgttcg gccctctacg tggggacct tgcgggtct gtctttcttg     1200 tcggtcaact gttcaccttc tctcccaggc gccactggac gacgcaagac tgcaattgtt   1260
ctatctatcc cggccatata acgggtcacc gcatggcatg ggatatgatg atgaactggt   1320
cccctacgac ggcgttggta gtagctcagc tgctccggat cccacaagcc atcttggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aagtgccgcc cgcgccacgg ctggatttgc tggcctcttc acaccaggcg   1560
ccaagcagaa catccagctg atcaacacca acggcagttg gcacatcaat gaacggcct    1620 tgaactgcaa tgatagccct aacaccggct ggctagcagg gcttttctat cacaacaaat   1680
tcaactcttc aggctgtccc gagaggttgg ccagctgccg accccttacc gattttgccc   1740
agggctgggg ccctatcagt tatgccaacg gaagcggccc cgaccaacgc ccctactgct   1800
ggcactaccc cccaaaacct tgtggtattg tgcccgcaaa gagcgtgtgt ggcccggtat   1860
attgcttcac tcccagcccc gtggtggtgg gaacgaccga caggtcgggc gcgcctacct   1920
acaactgggg tgaaaatgat acggacgtct tcgtccttaa caacaccagg ccaccgctgg   1980
gcaattggtt cggttgtacc tggatgaact caactggatt caccaaagtg tgcggagcgc   2040
ccccttgtaa catcggaggg gtgggcaaca acaccttgca ctgccccact gattgtttcc   2100
gcaagcatcc ggaagccacg tactctcggt gcggctccgg tcctggatt acacccaggt    2160 gcctggtcga ctacccgtat aggctttggc attatccttg taccatcaac tacaccatat   2220
tcaaagtcag gatgtacgtg ggagggggtcg agcacaggct ggaagctgcc tgcaactgga   2280
cgcggggcga acgttgtgat ctggaagaca gggacaggtc cgagctcagc ccgttgctgc   2340
tgtccaccac acagtggcag gtccttccgt gttccttcac gaccctgcca gccttgtcca   2400
ccggcctcat ccacctccac cagaacattg tggacgtgca gtacttgtac ggggtggggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580 cttttggagaa cctcgtaata tcaatgcag catccctggc cggacgcac ggtcttgtat     2640 ccttcctcgt gttcttctgc tttgcatggt atctgaaggg taagtgggtg cccggagcgg   2700
tctacgccct ctacggatg tggcctctcc tcctgctcct gttggcgttg ccccagcggg    2760
catacgcact ggacacggag gtggccgcgt cgtgtggcgg cgttgttctt gtcgggttaa   2820
tggcgctgac tctgtcacca tattacaagc gctatatcag ctggtgcttg tggtggcttc   2880
agtattttct gaccagagta gaagcgcaac tgcacgtgtg ggttccccccc ctcaacgtcc   2940 gagggggggcg cgacgccgtc atcttactca tgtgtgttgt acacccgact ctggtatttg   3000
```

-continued

```
acatcaccaa actactgctg gccgtcttcg gaccccttttg gattcttcaa gccagtttgc      3060
ttaaagtacc ctacttcgtg cgcgttcaag gccttctccg gatctgcgcg ctagcgcgga      3120
agatggccgg aggccattac gtgcaaatgg ccatcatcaa gttaggggcg cttactggca      3180
cctatgttta taaccatctc actcctcttc gggactgggc gcacaacggc ctgcgagatc      3240
tggccgtggc tgtggagcca gtcgtcttct cccaaatgga gaccaagctc atcacgtggg      3300
gggcagacac cgccgcgtgc ggtgacatca tcaacggctt gcccgtctcc gcccgtaggg      3360
gccgggagat actgctcgga ccagccgacg gaatggtctc caaggggtgg aggttgctgg      3420
cgcccatcac ggcgtacgcc cagcagacaa ggggcctcct agggtgtata atcaccagcc      3480
tgactggccg ggacaaaaac caagtggagg gtgaggtcca gattgtgtca actgctgccc      3540
aaactttcct ggcaacgtgc atcaatgggg tatgctggac tgtctaccac ggggccggaa      3600
cgaggaccat cgcatcaccc aagggtcctg ttatccagat gtataccaat gtggacaaag      3660
accttgtggg ctggcccgct cctcaaggtg cccgctcatt gacaccctgc acctgcggct      3720
cctcggacct ttacctggtc acgaggcacg ccgatgtcat tcccgtgcgc cggcggggtg      3780
atagcagggg cagcctgctt tcgccccggc ccatttccta cttgaaaggc tcctcggggg      3840
gtccgctgtt gtgcccgcg gacacgccg taggcatatt cagggccgcg gtgtgcaccc      3900
gtggagtggc taaggcggtg gactttatcc ctgtggagaa cctagagaca accatgaggt      3960
ccccggtgtt cacggacaac tcctctccac cagcagtgcc ccagagcttc caggtggccc      4020
acctgcatgc tcccaccggc agcggtaaga gcaccaaggt cccggctgca tacgcagctc      4080
agggctacaa ggtgctagtg ctcaacccct ctgttgctgc aacactgggc tttggtgctt      4140
acatgtccaa ggcccatggg atcgatccta acatcaggac cggggtgaga acaattacca      4200
ctggcagccc catcacgtac tccacctacg gcaagttcct tgccgacggc gggtgctcag      4260
ggggtgctta tgacataata atttgtgacg agtgccactc cacggatgcc acatccatct      4320
tgggcatcgg cactgtcctt gaccaagcag agactgcggg ggcgagactg gttgtgctcg      4380
ccaccgctac ccctccgggc tccgtcactg tgccccatcc taacatcgag gaggttgctc      4440
tgtccaccac cggagagatc ccttttttacg gcaaggctat ccccctcgag gtaatcaagg      4500
gggggagaca tctcatcttc tgtcactcaa agaagaagtg tgacgagctc gccgcaaagc      4560
tggtcgcatt gggcatcaat gccgtggcct actaccgcgg tcttgacgtg tctgtcatcc      4620
cgaccagcgg cgatgttgtc gtcgtggcaa ctgatgctct catgaccggc tataccggcg      4680
acttcgactc ggtgatagac tgcaacacgt gtgtcaccca gacagtcgat ttcagccttg      4740
accctacctt caccattgag acaaccacgc ttccccagga tgctgtctcc cgcactcaac      4800 gtcgggcag gactggcagg gggaagccag gcatctacag atttgtggca ccggggagc      4860 gccctccgg catgttcgac tcgtccgtcc tctgtgagtg ctatgacgcg ggctgtgctt      4920
ggtatgagct cacgccgcc gagactacag ttaggctacg agcgtacatg aacacccgg      4980 ggcttcccgt gtgccaggac catcttgaat tttgggaggg cgtctttacg ggcctcactc      5040
atatagatgc ccacttccta tcccagacaa agcagagtgg ggagaacttt ccttacctgg      5100
tagcgtacca agccaccgtg tgcgctaggg ctcaagcccc tccccatcg tgggaccaga      5160 tgtggaagtg tttgatccgc ctcaaaccca ccctccatgg gccaacaccc ctgctataca      5220
gactgggcgc tgttcagaat gaagtcaccc tgacgcaccc aatcaccaaa tacatcatga      5280
catgcatgtc ggccgacctg gaggtcgtca cgagcacctg ggtgctcgtt ggcggcgtcc      5340
tggctgcttt ggccgcgtat tgcctgtcaa caggctgcgt ggtcatagtg gcagggttg      5400
```

```
tcttgtccgg gaagccggca attataccty acagggaagt tctctaccgg gagttcgatg    5460
agatggaaga gtgctctcag cacttaccgt acatcgagca agggatgatg ctcgctgagc    5520
agttcaagca gaaggccctc ggcctcctgc agaccgcgtc ccgtcaggca gaggttatcg    5580
cccctgctgt ccagaccaac tggcaaaaac tcgagacctt ctgggcgaag catatgtgga    5640
acttcatcag tgggatacaa tacttggcgg gcctgtcaac gttgcctggt aaccccgcca    5700
ttgcttcatt gatggctttt acagctgctg tcaccagccc actaaccact agccaaaccc    5760
tcctcttcaa catattgggg gggtgggtgg ctgcccagct cgccgccccc ggtgccgcta    5820
ccgcctttgt gggcgctggc ttagctgcg ccgccatcgg cagtgttgga ctggggaagg     5880
tcctcgtgga cattcttgca gggtatggcg cgggcgtggc gggagctctt gtagcattca    5940
agatcatgag cggtgaggtc ccctccacgg aggacctggt caatctgctg cccgccatcc    6000
tctcgcctgg agcccttgta gtcggtgtgg tctgcgcagc aatactgcgc cggcacgttg    6060
gcccgggcga gggggcagtg caatggatga accggctaat agccttcgcc tcccggggga    6120
accatgtttc ccccacgcac tacgtgccgg agagcgatga agctgcccgc gtcactgcca    6180
tactcagcag cctcactgta acccagctcc tgaggcgact gcaccagtgg ataagctcgg    6240
agtgtaccac tccatgctcc ggttcctggc taagggacat ctgggactgg atatgcgagg    6300
tgctgagcga cttaagacc tggctaaaag ccaagctcat gccacaactg cctgggattc     6360
cctttgtgtc ctgccagcgc gggtataggg gggtctggcg aggggacggc atcatgcaca    6420
ctcgctgcca ctgtggagct gagatcactg gacatgtcaa aaacgggacg atgaggatcg    6480
tcggtcctag gacctgcagg aacatgtgga gtgggacctt ccccattaac gcctacacca    6540
cgggcccctg tactcccctt cctgcgccga actataagtt cgcgctgtgg agggtgtctg    6600
cagaggaata cgtggagata aggcaggtgg gggacttcca ctacgtgacg ggtatgacta    6660
ctgacaatct taaatgcccg tgccaggtcc catcgcccga atttttcaca gaattggacg    6720
gggtgcgcct acataggttt gcgccccctt gcaagccctt gctgcgggag gaggtatcat    6780
tcagagtagg actccacgag tacccggtgg ggtcgcaatt accttgcgag cccgaaccgg    6840
acgtggccgt gttgacgtcc atgctcactg atcctccca taacagca gaggcggccg      6900 ggagaaggtt ggcgagggga tcaccccctt ctgtggccag ctcctcggct agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcggaggag gatgagcggg    7140
agatctccgt acccgcagaa atcctgcgga agtctcggag attcgcccag ccctgccca    7200 tttgggcgcg gccggactat aaccccccgc tgatagagac gtggaaaaag cctgactacg    7260
aaccacctgt ggtccatggc tgcccgcttc cacctccaca gtcccctcct gtgcctccgc    7320
ctcggaagaa gcgacggtg gtcctcaccg aatcaaccgt atctactgcc ttggccgagc     7380
ttgccaccaa aagtttggc agctcctcaa cttccggtat tacgggcgac aatacgacaa     7440
catcctctga gccgccct tctggctgcc cccagactc cgacgctgag tcctattctt       7500
ccatgccccc cctggagggg gagcctgggg atccggatct cagcgacggg tcatggtcga    7560
cggtcagtag tgaggccgac acggaggatg tcgtgtgctg ctcaatgtct tattcctgga    7620
caggcgcact cgtcacccg tgcgccgcgg aagaacaaaa actgcccatc aacgcactga    7680
gcaactcgtt gctacgtcat cacaatctgg tgtattccac cacctcacgc agtgcttgcc    7740
aaaggcagaa gaaagtcaca tttgacagac tgcaagttct ggacagccat taccaggacg    7800
```

```
tgctcaagga ggttaaagca gcggcgtcaa aagtgaaggc taacttgcta tccgtagagg    7860
aagcttgcag cctgacgccc ccacactcag ccaaatccaa gtttggctat ggggcaaaag    7920
acgtccgttg ccatgccaga aaggccgtaa accacatcaa ctccgtgtgg aaagaccttc    7980
tggaagacag tgtaacacca atagacacta ccatcatggc taagaacgag gttttctgcg    8040
ttcagcctga aagggggggt cgtaagccag ctcgtctcat cgtgttcccc gacctgggtg    8100
tgcgcgtgtg cgagaagatg gccctgtacg acgtggttag caagctcccc ctggccgtga    8160
tgggaagctc ctacggattc caatactcac caggacagcg ggttgaattc ctcgtgcaag    8220
cgtggaagtc caagaagacc ccaatggggt tctcgtatga tacccgctgc tttgactcca    8280
cagtcactga gagcgacatc cgtacggagg aggcaatcta ccaatgttgt gacctggacc    8340
cccaagcccg cgtggccatc aagtccctca ctgagaggct ttatgttggg ggccctctta    8400
ccaattcaag gggggagaac tgcggctacc gcaggtgccg cgcgagcggc gtactgacaa    8460
ctagctgtgg taacaccctc acttgctaca tcaaggcccg agcagcctgt cgagccgcag    8520
ggctccagga ctgcaccatg ctcgtgtgtg cgacgacttt agtcgttatc tgtgaaagtg    8580
cgggggtcca ggaggacgcg gcgagcctga gagccttcac ggaggctatg accaggtact    8640
ccgcccccc cggggacccc ccacaaccag aatacgactt ggagctcata acatcatgct    8700
cctccaacgt gtcagtcgcc cacgacggcg ctggaaagag ggtctactac cttacccgtg    8760
acccctacaa ccccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggcccct gattgcgaga    8940
tctacggagc ctgctactcc atagaaccac tggatctacc tccaatcatt caaagactcc    9000
atggcctcag cgcatttcc ctccacagtt actctccagg tgaaatcaat agggtggccg    9060
catgcctcag gaaacttggg gtcccgccct tgcgagcttg gagacaccgg gcccggagcg    9120
tccgcgctag gcttctgtcc agaggaggca gggctgccat atgtggcaag tacctcttca    9180
actgggcagt aagaacaaag ctcaaactca ctccaatagc ggccgctggc cggctggact    9240
tgtccggctg gttcacggct ggctacagcg ggggagacat ttatcacagc gtgtctcatg    9300
cccggccccg ctggttctgg ttttgcctac tcctgcttgc tgcaggggta ggcatctacc    9360
tcctccccaa ccgatgaagg ttgggtaaa cactccggcc ttttaggcca tttcctgttt    9420
tttttttttt tttttttttt tttttttttt tttttttttt tttttttct tttttttttt    9480
tttcctttct tcttttcttt tttttaatg gtggctccat cttagcccta gtcacggcta    9540
gctgtgaaag gtccgtgagc cgcatgactg cagagagtgc tgatactggc ctctccgcag    9600
atcatgt                                                              9607
```

<210> SEQ ID NO 2
<211> LENGTH: 3011
<212> TYPE: PRT
<213> ORGANISM: Artificial Sequence
<220> FEATURE:
<223> OTHER INFORMATION: synthetic sequence

<400> SEQUENCE: 2

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30
```

```
Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
        210                 215                 220

Gly Cys Val Pro Cys Val Arg Glu Gly Asn Ala Ser Arg Cys Trp Val
225                 230                 235                 240

Ala Leu Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
        260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
        290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Ile Pro Gln Ala Ile Leu Asp Met Ile Ala Gly Ala His
        340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
        370                 375                 380

Thr His Val Thr Gly Gly Ser Ala Ala Arg Ala Thr Ala Gly Phe Ala
385                 390                 395                 400

Gly Leu Phe Thr Pro Gly Ala Lys Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Trp Leu Ala Gly Leu Phe Tyr His Asn Lys Phe Asn
        435                 440                 445
```

```
Ser Ser Gly Cys Pro Glu Arg Leu Ala Ser Cys Arg Pro Leu Thr Asp
450                 455                 460

Phe Ala Gln Gly Trp Gly Pro Ile Ser Tyr Ala Asn Gly Ser Gly Pro
465                 470                 475                 480

Asp Gln Arg Pro Tyr Cys Trp His Tyr Pro Lys Pro Cys Gly Ile
            485                 490                 495

Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Asn
        515                 520                 525

Trp Gly Glu Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Asn Ile Gly Val Gly Asn
            565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
            595                 600                 605

Val Asp Tyr Pro Tyr Arg Leu Trp His Tyr Pro Cys Thr Ile Asn Tyr
            610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
            725                 730                 735

Met Met Leu Leu Ile Ser Gln Ala Glu Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Lys Trp Val Pro
            770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
            835                 840                 845

Phe Leu Thr Arg Val Glu Ala Gln Leu His Val Trp Val Pro Pro Leu
850                 855                 860
```

```
Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Ile Cys Ala Leu Ala Arg Lys Met
                915                 920                 925

Ala Gly Gly His Tyr Val Gln Met Ala Ile Ile Lys Leu Gly Ala Leu
            930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Phe
                965                 970                 975

Ser Gln Met Glu Thr Lys Leu Ile Thr Trp Gly Ala Asp Thr Ala Ala
                980                 985                 990

Cys Gly Asp Ile Ile Asn Gly Leu  Pro Val Ser Ala Arg  Arg Gly Arg
                995                 1000                1005

Glu Ile  Leu Leu Gly Pro Ala  Asp Gly Met Val Ser  Lys Gly Trp
    1010                1015                1020

Arg Leu  Leu Ala Pro Ile Thr  Ala Tyr Ala Gln Gln  Thr Arg Gly
    1025                1030                1035

Leu Leu  Gly Cys Ile Ile Thr  Ser Leu Thr Gly Arg  Asp Lys Asn
    1040                1045                1050

Gln Val  Glu Gly Glu Val Gln  Ile Val Ser Thr Ala  Ala Gln Thr
    1055                1060                1065

Phe Leu  Ala Thr Cys Ile Asn  Gly Val Cys Trp Thr  Val Tyr His
    1070                1075                1080

Gly Ala  Gly Thr Arg Thr Ile  Ala Ser Pro Lys Gly  Pro Val Ile
    1085                1090                1095

Gln Met  Tyr Thr Asn Val Asp  Lys Asp Leu Val Gly  Trp Pro Ala
    1100                1105                1110

Pro Gln  Gly Ala Arg Ser Leu  Thr Pro Cys Thr Cys  Gly Ser Ser
    1115                1120                1125

Asp Leu  Tyr Leu Val Thr Arg  His Ala Asp Val Ile  Pro Val Arg
    1130                1135                1140

Arg Arg  Gly Asp Ser Arg Gly  Ser Leu Leu Ser Pro  Arg Pro Ile
    1145                1150                1155

Ser Tyr  Leu Lys Gly Ser Ser  Gly Gly Pro Leu Leu  Cys Pro Ala
    1160                1165                1170

Gly His  Ala Val Gly Ile Phe  Arg Ala Ala Val Cys  Thr Arg Gly
    1175                1180                1185

Val Ala  Lys Ala Val Asp Phe  Ile Pro Val Glu Asn  Leu Glu Thr
    1190                1195                1200

Thr Met  Arg Ser Pro Val Phe  Thr Asp Asn Ser Ser  Pro Pro Ala
    1205                1210                1215

Val Pro  Gln Ser Phe Gln Val  Ala His Leu His Ala  Pro Thr Gly
    1220                1225                1230

Ser Gly  Lys Ser Thr Lys Val  Pro Ala Ala Tyr Ala  Ala Gln Gly
    1235                1240                1245

Tyr Lys  Val Leu Val Leu Asn  Pro Ser Val Ala Ala  Thr Leu Gly
    1250                1255                1260
```

```
Phe Gly Ala Tyr Met Ser Lys Ala His Gly Ile Asp Pro Asn Ile
1265                1270                1275
Arg Thr Gly Val Arg Thr Ile Thr Thr Gly Ser Pro Ile Thr Tyr
1280                1285                1290
Ser Thr Tyr Gly Lys Phe Leu Ala Asp Gly Gly Cys Ser Gly Gly
1295                1300                1305
Ala Tyr Asp Ile Ile Ile Cys Asp Glu Cys His Ser Thr Asp Ala
1310                1315                1320
Thr Ser Ile Leu Gly Ile Gly Thr Val Leu Asp Gln Ala Glu Thr
1325                1330                1335
Ala Gly Ala Arg Leu Val Val Leu Ala Thr Ala Thr Pro Pro Gly
1340                1345                1350
Ser Val Thr Val Pro His Pro Asn Ile Glu Glu Val Ala Leu Ser
1355                1360                1365
Thr Thr Gly Glu Ile Pro Phe Tyr Gly Lys Ala Ile Pro Leu Glu
1370                1375                1380
Val Ile Lys Gly Gly Arg His Leu Ile Phe Cys His Ser Lys Lys
1385                1390                1395
Lys Cys Asp Glu Leu Ala Ala Lys Leu Val Ala Leu Gly Ile Asn
1400                1405                1410
Ala Val Ala Tyr Tyr Arg Gly Leu Asp Val Ser Val Ile Pro Thr
1415                1420                1425
Ser Gly Asp Val Val Val Ala Thr Asp Ala Leu Met Thr Gly
1430                1435                1440
Tyr Thr Gly Asp Phe Asp Ser Val Ile Asp Cys Asn Thr Cys Val
1445                1450                1455
Thr Gln Thr Val Asp Phe Ser Leu Asp Pro Thr Phe Thr Ile Glu
1460                1465                1470
Thr Thr Thr Leu Pro Gln Asp Ala Val Ser Arg Thr Gln Arg Arg
1475                1480                1485
Gly Arg Thr Gly Arg Gly Lys Pro Gly Ile Tyr Arg Phe Val Ala
1490                1495                1500
Pro Gly Glu Arg Pro Ser Gly Met Phe Asp Ser Ser Val Leu Cys
1505                1510                1515
Glu Cys Tyr Asp Ala Gly Cys Ala Trp Tyr Glu Leu Thr Pro Ala
1520                1525                1530
Glu Thr Thr Val Arg Leu Arg Ala Tyr Met Asn Thr Pro Gly Leu
1535                1540                1545
Pro Val Cys Gln Asp His Leu Glu Phe Trp Glu Gly Val Phe Thr
1550                1555                1560
Gly Leu Thr His Ile Asp Ala His Phe Leu Ser Gln Thr Lys Gln
1565                1570                1575
Ser Gly Glu Asn Phe Pro Tyr Leu Val Ala Tyr Gln Ala Thr Val
1580                1585                1590
Cys Ala Arg Ala Gln Ala Pro Pro Ser Trp Asp Gln Met Trp
1595                1600                1605
Lys Cys Leu Ile Arg Leu Lys Pro Thr Leu His Gly Pro Thr Pro
1610                1615                1620
Leu Leu Tyr Arg Leu Gly Ala Val Gln Asn Glu Val Thr Leu Thr
1625                1630                1635
His Pro Ile Thr Lys Tyr Ile Met Thr Cys Met Ser Ala Asp Leu
1640                1645                1650
```

-continued

```
Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Val Val Leu Ser Gly Lys Pro Ala Ile Ile Pro Asp Arg
1685                1690                1695

Glu Val Leu Tyr Arg Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg Gln Ala
1730                1735                1740

Glu Val Ile Ala Pro Ala Val Gln Thr Asn Trp Gln Lys Leu Glu
1745                1750                1755

Thr Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Ser Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Ala Ile Leu Ser Ser Leu Thr Val
1940                1945                1950

Thr Gln Leu Leu Arg Arg Leu His Gln Trp Ile Ser Ser Glu Cys
1955                1960                1965

Thr Thr Pro Cys Ser Gly Ser Trp Leu Arg Asp Ile Trp Asp Trp
1970                1975                1980

Ile Cys Glu Val Leu Ser Asp Phe Lys Thr Trp Leu Lys Ala Lys
1985                1990                1995

Leu Met Pro Gln Leu Pro Gly Ile Pro Phe Val Ser Cys Gln Arg
2000                2005                2010

Gly Tyr Arg Gly Val Trp Arg Gly Asp Gly Ile Met His Thr Arg
2015                2020                2025

Cys His Cys Gly Ala Glu Ile Thr Gly His Val Lys Asn Gly Thr
2030                2035                2040
```

```
Met Arg Ile Val Gly Pro Arg Thr Cys Arg Asn Met Trp Ser Gly
2045                     2050                2055

Thr Phe Pro Ile Asn Ala Tyr Thr Thr Gly Pro Cys Thr Pro Leu
2060                     2065                2070

Pro Ala Pro Asn Tyr Lys Phe Ala Leu Trp Arg Val Ser Ala Glu
2075                     2080                2085

Glu Tyr Val Glu Ile Arg Gln Val Gly Asp Phe His Tyr Val Thr
2090                     2095                2100

Gly Met Thr Thr Asp Asn Leu Lys Cys Pro Cys Gln Val Pro Ser
2105                     2110                2115

Pro Glu Phe Phe Thr Glu Leu Asp Gly Val Arg Leu His Arg Phe
2120                     2125                2130

Ala Pro Pro Cys Lys Pro Leu Leu Arg Glu Glu Val Ser Phe Arg
2135                     2140                2145

Val Gly Leu His Glu Tyr Pro Val Gly Ser Gln Leu Pro Cys Glu
2150                     2155                2160

Pro Glu Pro Asp Val Ala Val Leu Thr Ser Met Leu Thr Asp Pro
2165                     2170                2175

Ser His Ile Thr Ala Glu Ala Ala Gly Arg Arg Leu Ala Arg Gly
2180                     2185                2190

Ser Pro Pro Ser Val Ala Ser Ser Ser Ala Ser Gln Leu Ser Ala
2195                     2200                2205

Pro Ser Leu Lys Ala Thr Cys Thr Ala Asn His Asp Ser Pro Asp
2210                     2215                2220

Ala Glu Leu Ile Glu Ala Asn Leu Leu Trp Arg Gln Glu Met Gly
2225                     2230                2235

Gly Asn Ile Thr Arg Val Glu Ser Glu Asn Lys Val Val Ile Leu
2240                     2245                2250

Asp Ser Phe Asp Pro Leu Val Ala Glu Glu Asp Glu Arg Glu Ile
2255                     2260                2265

Ser Val Pro Ala Glu Ile Leu Arg Lys Ser Arg Arg Phe Ala Gln
2270                     2275                2280

Ala Leu Pro Ile Trp Ala Arg Pro Asp Tyr Asn Pro Pro Leu Ile
2285                     2290                2295

Glu Thr Trp Lys Lys Pro Asp Tyr Glu Pro Pro Val Val His Gly
2300                     2305                2310

Cys Pro Leu Pro Pro Gln Ser Pro Pro Val Pro Pro Pro Arg
2315                     2320                2325

Lys Lys Arg Thr Val Val Leu Thr Glu Ser Thr Val Ser Thr Ala
2330                     2335                2340

Leu Ala Glu Leu Ala Thr Lys Ser Phe Gly Ser Ser Ser Thr Ser
2345                     2350                2355

Gly Ile Thr Gly Asp Asn Thr Thr Thr Ser Ser Glu Pro Ala Pro
2360                     2365                2370

Ser Gly Cys Pro Pro Asp Ser Asp Ala Glu Ser Tyr Ser Ser Met
2375                     2380                2385

Pro Pro Leu Glu Gly Glu Pro Gly Asp Pro Asp Leu Ser Asp Gly
2390                     2395                2400

Ser Trp Ser Thr Val Ser Ser Glu Ala Asp Thr Glu Asp Val Val
2405                     2410                2415

Cys Cys Ser Met Ser Tyr Ser Trp Thr Gly Ala Leu Val Thr Pro
2420                     2425                2430
```

```
Cys Ala Ala Glu Glu Gln Lys Leu Pro Ile Asn Ala Leu Ser Asn
2435                2440                2445

Ser Leu Leu Arg His His Asn Leu Val Tyr Ser Thr Thr Ser Arg
2450                2455                2460

Ser Ala Cys Gln Arg Gln Lys Lys Val Thr Phe Asp Arg Leu Gln
2465                2470                2475

Val Leu Asp Ser His Tyr Gln Asp Val Leu Lys Glu Val Lys Ala
2480                2485                2490

Ala Ala Ser Lys Val Lys Ala Asn Leu Leu Ser Val Glu Glu Ala
2495                2500                2505

Cys Ser Leu Thr Pro Pro His Ser Ala Lys Ser Lys Phe Gly Tyr
2510                2515                2520

Gly Ala Lys Asp Val Arg Cys His Ala Arg Lys Ala Val Asn His
2525                2530                2535

Ile Asn Ser Val Trp Lys Asp Leu Leu Glu Asp Ser Val Thr Pro
2540                2545                2550

Ile Asp Thr Thr Ile Met Ala Lys Asn Glu Val Phe Cys Val Gln
2555                2560                2565

Pro Glu Lys Gly Gly Arg Lys Pro Ala Arg Leu Ile Val Phe Pro
2570                2575                2580

Asp Leu Gly Val Arg Val Cys Glu Lys Met Ala Leu Tyr Asp Val
2585                2590                2595

Val Ser Lys Leu Pro Leu Ala Val Met Gly Ser Ser Tyr Gly Phe
2600                2605                2610

Gln Tyr Ser Pro Gly Gln Arg Val Glu Phe Leu Val Gln Ala Trp
2615                2620                2625

Lys Ser Lys Lys Thr Pro Met Gly Phe Ser Tyr Asp Thr Arg Cys
2630                2635                2640

Phe Asp Ser Thr Val Thr Glu Ser Asp Ile Arg Thr Glu Glu Ala
2645                2650                2655

Ile Tyr Gln Cys Cys Asp Leu Asp Pro Gln Ala Arg Val Ala Ile
2660                2665                2670

Lys Ser Leu Thr Glu Arg Leu Tyr Val Gly Gly Pro Leu Thr Asn
2675                2680                2685

Ser Arg Gly Glu Asn Cys Gly Tyr Arg Arg Cys Arg Ala Ser Gly
2690                2695                2700

Val Leu Thr Thr Ser Cys Gly Asn Thr Leu Thr Cys Tyr Ile Lys
2705                2710                2715

Ala Arg Ala Ala Cys Arg Ala Ala Gly Leu Gln Asp Cys Thr Met
2720                2725                2730

Leu Val Cys Gly Asp Asp Leu Val Val Ile Cys Glu Ser Ala Gly
2735                2740                2745

Val Gln Glu Asp Ala Ala Ser Leu Arg Ala Phe Thr Glu Ala Met
2750                2755                2760

Thr Arg Tyr Ser Ala Pro Pro Gly Asp Pro Pro Gln Pro Glu Tyr
2765                2770                2775

Asp Leu Glu Leu Ile Thr Ser Cys Ser Ser Asn Val Ser Val Ala
2780                2785                2790

His Asp Gly Ala Gly Lys Arg Val Tyr Tyr Leu Thr Arg Asp Pro
2795                2800                2805

Thr Thr Pro Leu Ala Arg Ala Ala Trp Glu Thr Ala Arg His Thr
2810                2815                2820
```

```
Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asp Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
    2915                2920                2925

Ala Arg Leu Leu Ser Arg Gly Gly Arg Ala Ala Ile Cys Gly Lys
    2930                2935                2940

Tyr Leu Phe Asn Trp Ala Val Arg Thr Lys Leu Lys Leu Thr Pro
    2945                2950                2955

Ile Ala Ala Ala Gly Arg Leu Asp Leu Ser Gly Trp Phe Thr Ala
    2960                2965                2970

Gly Tyr Ser Gly Gly Asp Ile Tyr His Ser Val Ser His Ala Arg
    2975                2980                2985

Pro Arg Trp Phe Trp Phe Cys Leu Leu Leu Leu Ala Ala Gly Val
    2990                2995                3000

Gly Ile Tyr Leu Leu Pro Asn Arg
    3005                3010

<210> SEQ ID NO 3
<211> LENGTH: 27
<212> TYPE: PRT
<213> ORGANISM: Artificial Sequence
<220> FEATURE:
<223> OTHER INFORMATION: synthetic sequence

<400> SEQUENCE: 3

Glu Thr His Val Thr Gly Gly Ser Ala Ala Arg Ala Thr Ala Gly Phe
1               5                   10                  15

Ala Gly Leu Phe Thr Pro Gly Ala Lys Gln Asn
            20                  25

<210> SEQ ID NO 4
<211> LENGTH: 10
<212> TYPE: PRT
<213> ORGANISM: Artificial Sequence
<220> FEATURE:
<223> OTHER INFORMATION: synthetic sequence

<400> SEQUENCE: 4

Lys Leu Val Ala Leu Gly Ile Asn Ala Val
1               5                   10

<210> SEQ ID NO 5
<211> LENGTH: 9607
<212> TYPE: DNA
<213> ORGANISM: Artificial Sequence
<220> FEATURE:
<223> OTHER INFORMATION: synthetic sequence
```

```
<400> SEQUENCE: 5
gccagccccc tgatgggggc gacactccac catgaatcac tccccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gataaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag gaagacttcc gagcggtcgc aacctcgagg tagacgtcag cctatcccca     540
aggcgcgtcg gcccgagggc aggacctggg ctcagcccgg gtaccttgg ccctctatg      600 gcaatgaggg ctgcgggtgg gcgggatggc tcctgtctcc ccgtggctct cggcctagct     660
ggggccccac agaccccgg cgtaggtcgc gcaatttggg taaggtcatc gatacccta      720 cgtgcggctt cgccgacctc atggggtaca taccgctcgt cggcgcccct cttggaggcg     780
ctgccagggc cctggcgcat ggcgtccggg ttctggaaga cggcgtgaac tatgcaacag     840
ggaaccttcc tggttgctct ttctctatct tccttctggc cctgctctct tgcctgactg     900
tgcccgcttc agcctaccaa gtgcgcaact cctcggggct ttaccatgtc accaatgatt     960
gccctaactc gagtattgtg tacgaggcgg ccgatgccat cctgcacact ccggggtgtg    1020
tcccttgcgt tcgcgagggt aacgcctcga ggtgttgggt ggcgatgacc ccacggtgg     1080 ccaccaggga cggcaaaactc cccacaacgc agcttcgacg tcacatcgat ctgcttgtcg    1140
ggagcgccac cctctgttcg gccctctacg tgggggacct gtgcgggtct gtctttcttg    1200
tcggtcaact gttcaccttc tctcccaggc gccactggac gacgcaagac tgcaattgtt    1260
ctatctatcc cggccatata acgggtcacc gcatggcatg ggatatgatg atgaactggt    1320
cccctacgac ggcgttggta gtagctcagc tgctccggat cccacaagcc atcttggaca    1380
tgatcgctgg tgctcactgg ggagtcctgg cgggcatagc gtatttctcc atggtgggga    1440
actgggcgaa ggtcctggta gtgctgctgc tatttgccgg cgtcgacgcg gaaacccacg    1500
tcaccggggg aagtgccgcc cgcgccacgg ctggatttgc tggcctcttc acaccaggcg    1560
ccaagcagaa catccagctg atcaacacca acggcagttg gcacatcaat agcacggcct    1620
tgaactgcaa tgatagcctt aacaccggct ggctagcagg gcttttctat cacaacaaat    1680
tcaactcttc aggctgtccc gagaggttgg ccagctgccg acccttacc gattttgccc     1740 agggctgggg ccctatcagt tatgccaacg gaagcggccc cgaccaacgc ccctactgct    1800
ggcactaccc cccaaaacct tgtggtattg tgcccgcaaa gagcgtgtgt ggcccggtat    1860
attgcttcac tccagccccc gtggtggtgg gaacgaccga caggtcgggc gcgcctacct    1920
acaactgggg tgaaaatgat acggacgtct tcgtccttaa caacaccagg ccaccgctgg    1980
gcaattggtt cggttgtacc tggatgaact caactggatt caccaaagtg tgcggagcgc    2040 cccccttgtga catcggaggg gtgggcaaca acaccttgca ctgccccact gattgtttcc    2100
gcaagcatcc ggaagccacg tactctcggt gcggctccgg tcctggatt acacccaggt     2160 gcctggtcga ctacccgtat aggctttggc attatccttg taccatcaac tacaccatat    2220
tcaaagtcag gatgtacgtg ggaggggtcg agcacaggct ggaagctgcc tgcaactgga    2280 cgcgggggcga acgttgtgat ctggaagaca gggacaggtc cgagctcagc ccgttgctgc    2340
```

-continued

```
tgtccaccac acagtggcag gtccttccgt gttccttcac gaccctgcca gccttgtcca    2400
ccggcctcat ccacctccac cagaacattg tggacgtgca gtacttgtac ggggtggggt    2460
caagcatcgc gtcctgggcc attaagtggg agtacgtcgt tctcctgttc cttctgcttg    2520
cagacgcgcg cgtctgctcc tgcttgtgga tgatgttact catatcccaa gcggaggcgg    2580 cttttggagaa cctcgtaata ctcaatgcag catccctggc cgggacgcac ggtcttgtat    2640
ccttcctcgt gttcttctgc tttgcatggt atctgaaggg taagtgggtg cccggagcgg    2700
tctacgccct ctacgggatg tggcctctcc tcctgctcct gttggcgttg ccccagcggg    2760
catacgcact ggacacggag gtggccgcgt cgtgtggcgg cgttgttctt gtcgggttaa    2820
tggcgctgac tctgtcacca tattacaagc gctatatcag ctggtgcttg tggtggcttc    2880
agtattttct gaccagagta gaagcgcaac tgcacgtgtg ggttccccc ctcaacgtcc      2940 gagggggggcg cgacgccgtc atcttactca tgtgtgttgt acacccgact ctggtatttg   3000
acatcaccaa actactgctg gccgtcttcg gacccctttg gattcttcaa gccagtttgc    3060
ttaaagtacc ctacttcgtg cgcgttcaag gccttctccg gatctgcgcg ctagcgcgga    3120
agatggccgg aggccattac gtgcaaatgg ccatcatcaa gttaggggcg cttactggca    3180
cctatgttta taaccatctc actcctcttc gggactgggc gcacaacggc ctgcgagatc    3240
tggccgtggc tgtggagcca gtcgtcttct cccaaatgga gaccaagctc atcacgtggg    3300
gggcagacac cgccgcgtgc ggtgacatca tcaacggctt gccgtctcc gcccgtaggg     3360 gccgggagat actgctcgga ccagccgacg gaatggtctc caaggggtgg aggttgctgg    3420
cgcccatcac ggcgtacgcc cagcagacaa ggggcctcct agggtgtata atcaccagcc    3480
tgactggccg ggacaaaaac caagtggagg gtgaggtcca gattgtgtca actgctgccc    3540
aaactttcct ggcaacgtgc atcaatgggg tatgctggac tgtctaccac ggggccggaa    3600
cgaggaccat cgcatcaccc aagggtcctg ttatccagat gtataccaat gtggacaaag    3660
accttgtggg ctggccccgct cctcaaggtg cccgctcatt gacaccctgc acctgcggct    3720
cctcggacct ttacctggtc acgaggcacg ccgatgtcat tcccgtgcgc cggcggggtg    3780
atagcagggg cagcctgctt tcgccccggc ccatttccta cttgaaaggc tcctcggggg    3840
gtccgctgtt gtgccccgcg ggacacgccg taggcatatt cagggccgcg tgtgcacccc    3900
gtggagtggc taaggcggtg gactttatcc ctgtggagaa cctagagaca accatgaggt    3960
ccccggtgtt cacggacaac tcctctccac cagcagtgcc ccagagcttc caggtggccc    4020
acctgcatgc tcccaccggc agcggtaaga gcaccaaggt cccggctgca tacgcagctc    4080
agggctacaa ggtgctagtg ctcaacccct ctgttgctgc aacactgggc tttggtgctt    4140
acatgtccaa ggcccatggg atcgatccta acatcaggac cggggtgaga acaattacca    4200
ctggcagccc catcacgtac tccacctacg gcaagttcct tgccgacggc gggtgctcag    4260
ggggtgctta tgacataata atttgtgacg agtgccactc cacggatgcc acatccatct    4320
tgggcatcgg cactgtcctt gaccaagcag agactgcggg ggcgagactg gttgtgctcg    4380
ccaccgctac ccctccgggc tccgtcactg tgccccatcc taacatcgag gaggttgctc    4440
tgtccaccac cggagagatc ccttttttacg gcaaggctat cccctcgag gtaatcaagg     4500 gggggagaca tctcatcttc tgtcactcaa agaagaagtg tgacgagctc gccgcaaagc    4560
tggtcgcatt gggcatcaat gccgtggcct actaccgcgg tcttgacgtg tctgtcatcc    4620
cgaccagcgc cgatgttgtc gtcgtggcaa ctgatgctct catgaccggc tataccggcg    4680
acttcgactc ggtgatagac tgcaacacgt gtgtcaccca gacagtcgat ttcagccttg    4740
```

```
accctacctt caccattgag acaaccacgc ttccccagga tgctgtctcc cgcactcaac    4800
gtcggggcag gactggcagg gggaagccag gcatctacag atttgtggca ccggggagc     4860 gcccctccgg catgttcgac tcgtccgtcc tctgtgagtg ctatgacgcg ggctgtgctt    4920
ggtatgagct cacgcccgcc gagactcag ttaggctacg agcgtacatg aacaccccgg     4980
ggcttcccgt gtgccaggac catcttgaat tttgggaggg cgtctttacg ggcctcactc    5040
atatagatgc ccacttccta tcccagacaa agcagagtgg ggagaacttt ccttacctgg    5100
tagcgtacca agccaccgtg tgcgctaggg ctcaagcccc tccccatcg tgggaccaga     5160 tgtggaagtg tttgatccgc ctcaaaccca ccctccatgg gccaacaccc ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgcttt ggccgcgtat tgcctgtcaa caggctgcgt ggtcatagtg ggcagggttg    5400
tcttgtccgg gaagccggca attatacctg acagggaagt tctctaccgg gagttcgatg    5460
agatggaaga gtgctctcag cacttaccgt acatcgagca agggatgatg ctcgctgagc    5520
agttcaagca gaaggccctc ggcctcctgc agaccgcgtc ccgtcaggca gaggttatcg    5580
cccctgctgt ccagaccaac tggcaaaaac tcgagacctt ctgggcgaag catatgtgga    5640
acttcatcag tgggatacaa tacttggcgg gcctgtcaac gttgcctggt aaccccgcca    5700
ttgcttcatt gatggctttt acagctgctg tcaccagccc actaaccact agccaaaccc    5760
tcctcttcaa catattgggg gggtgggtgg ctgcccagct cgccgccccc ggtgccgcta    5820
ccgcctttgt gggcgctggc ttagctgcg ccgccatcgg cagtgttgga ctggggaagg     5880
tcctcgtgga cattcttgca gggtatggcg cgggcgtggc gggagctctt gtagcattca    5940
agatcatgag cggtgaggtc ccctccacgg aggacctggt caatctgctg cccgccatcc    6000
tctcgcctgg agcccttgta gtcggtgtgg tctgcgcagc aatactgcgc cggcacgttg    6060
gcccgggcga gggggcagtg caatggatga accggctaat agccttcgcc tcccggggga    6120
accatgtttc ccccacgcac tacgtgccgg agagcgatgc agctgcccgc gtcactgcca    6180
tactcagcag cctcactgta acccagctcc tgaggcgact gcaccagtgg ataagctcgg    6240
agtgtaccac tccatgctcc ggttcctggc taagggacat ctgggactgg atatgcgagg    6300
tgctgagcga ctttaagacc tggctaaaag ccaagctcat gccacaactg cctgggattc    6360
cctttgtgtc ctgccagcgc gggtataggg gggtctggcg aggggacggc atcatgcaca    6420
ctcgctgcca ctgtggagct gagatcactg gacatgtcaa aaacgggacg atgaggatcg    6480
tcggtcctag gacctgcagg aacatgtgga gtgggacctt ccccattaac gcctacacca    6540
cgggcccctg tactccccct cctgcgccga actataagtt cgcgctgtgg agggtgtctg    6600
cagaggaata cgtggagata aggcaggtgg gggacttcca ctacgtgacg ggtatgacta    6660
ctgacaatct taaatgcccg tgccaggtcc catcgcccga ttttttcaca gaattggacg    6720
gggtgcgcct acataggttt gcgcccccct gcaagccctt gctgcgggag gaggtatcat    6780
tcagagtagg actccacgag tacccggtgg ggtcgcaatt accttgcgag cccgaaccgg    6840
acgtggccgt gttgacgtcc atgctcactg atcccctccca tataacagca gaggcggccg    6900
ggagaaggtt ggcgagggga tcacccccctt ctgtggccag ctcctcggct agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcggaggag gatgagcggg    7140
```

-continued

```
agatctccgt acccgcagaa atcctgcgga agtctcggag attcgcccag gccctgccca    7200
tttgggcgcg gccggactat aaccccccgc tgatagagac gtggaaaaag cctgactacg    7260
aaccacctgt ggtccatggc tgcccgcttc cacctccaca gtcccctcct gtgcctccgc    7320
ctcggaagaa gcgacggtg gtcctcaccg aatcaaccgt atctactgcc ttggccgagc    7380
ttgccaccaa aagttttggc agctcctcaa cttccggtat tacgggcgac aatacgacaa    7440
catcctctga gcccgcccct tctggctgcc cccagactc cgacgctgag tcctattctt    7500
ccatgccccc cctggagggg gagcctgggg atccggatct cagcgacggg tcatggtcga    7560
cggtcagtag tgaggccgac acggaggatg tcgtgtgctg ctcaatgtct tattcctgga    7620
caggcgcact cgtcaccccg tgcgccgcgg aagaacaaaa actgcccatc aacgcactga    7680
gcaactcgtt gctacgtcat cacaatctgg tgtattccac cacctcacgc agtgcttgcc    7740
aaaggcagaa gaaagtcaca tttgacagac tgcaagttct ggacagccat taccaggacg    7800
tgctcaagga ggttaaagca gcggcgtcaa aagtgaaggc taacttgcta tccgtagagg    7860
aagcttgcag cctgacgccc ccacactcag ccaaatccaa gtttggctat ggggcaaaag    7920
acgtccgttg ccatgccaga aaggccgtaa accacatcaa ctccgtgtgg aaagaccttc    7980
tggaagacag tgtaacacca atagacacta ccatcatggc taagaacgag gttttctgcg    8040
ttcagcctga aagggggggt cgtaagccag ctcgtctcat cgtgttcccc gacctgggtg    8100
tgcgcgtgtg cgagaagatg gccctgtacg acgtggttag caagctcccc ctggccgtga    8160
tgggaagctc ctacggattc caatactcac caggacagcg ggttgaattc ctcgtgcaag    8220
cgtggaagtc caagaagacc ccaatggggt tctcgtatga tacccgctgc tttgactcca    8280
cagtcactga gagcgacatc cgtacggagg aggcaatcta ccaatgttgt gacctggacc    8340
cccaagcccg cgtggccatc aagtccctca ctgagaggct ttatgttggg ggccctctta    8400
ccaattcaag gggggagaac tgcggctacc gcaggtgccg cgcgagcggc gtactgacaa    8460
ctagctgtgg taacaccctc acttgctaca tcaaggcccg agcagcctgt cgagccgcag    8520
ggctccagga ctgcaccatg ctcgtgtgtg cgacgactt agtcgttatc tgtgaaagtg    8580
cgggggtcca ggaggacgcg gcgagcctga gagccttcac ggaggctatg accaggtact    8640
ccgcccccc cggggacccc ccacaaccag aatacgactt ggagctcata acatcatgct    8700
cctccaacgt gtcagtcgcc cacgacgcg ctggaaagag ggtctactac cttacccgtg    8760
accctacaac ccccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggcccctt gattgcgaga    8940
tctacgagc ctgctactcc atagaaccac tggatctacc tccaatcatt caaagactcc    9000
atggcctcag cgcattttca ctccacagtt actctccagg tgaaatcaat agggtggccg    9060
catgcctcag gaaacttggg gtcccgccct tgcgagcttg gagacaccgg gcccggagcg    9120
tccgcgctag gcttctgtcc agaggaggca gggctgccat atgtggcaag tacctcttca    9180
actgggcagt aagaacaaag ctcaaactca ctccaatagc ggccgctggc cggctggact    9240
tgtccggctg gttcacggct ggctacagcg ggggagacat ttatcacagc gtgtctcatg    9300
cccggccccg ctggttctgg ttttgcctac tcctgcttgc tgcaggggta ggcatctacc    9360
tcctccccaa ccgatgaagg ttgggggtaaa cactccggcc ttttaggcca tttcctgttt    9420
tttttttttt tttttttttt tttttttttt tttttttttt tttttttct tttttttttt    9480
tttcctttct tcttttttctt tttttaatg gtggctccat cttagcccta gtcacggcta    9540
```

```
gctgtgaaag gtccgtgagc cgcatgactg cagagagtgc tgatactggc ctctccgcag    9600
atcatgt                                                              9607
```

<210> SEQ ID NO 6
<211> LENGTH: 3011
<212> TYPE: PRT
<213> ORGANISM: Artificial Sequence
<220> FEATURE:
<223> OTHER INFORMATION: synthetic sequence

<400> SEQUENCE: 6

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Ile Pro Gln Ala Ile Leu Asp Met Ile Ala Gly Ala His
            340                 345                 350
```

-continued

```
Trp Gly Val Leu Ala Gly Ile Ala Tyr Phe Ser Met Val Gly Asn Trp
            355                 360                 365
Ala Lys Val Leu Val Leu Leu Phe Ala Gly Val Asp Ala Glu
    370                 375                 380
Thr His Val Thr Gly Gly Ser Ala Ala Arg Ala Thr Ala Gly Phe Ala
385                 390                 395                 400
Gly Leu Phe Thr Pro Gly Ala Lys Gln Asn Ile Gln Leu Ile Asn Thr
                405                 410                 415
Asn Gly Ser Trp His Ile Asn Ser Thr Ala Leu Asn Cys Asn Asp Ser
            420                 425                 430
Leu Asn Thr Gly Trp Leu Ala Gly Leu Phe Tyr His Asn Lys Phe Asn
        435                 440                 445
Ser Ser Gly Cys Pro Glu Arg Leu Ala Ser Cys Arg Pro Leu Thr Asp
    450                 455                 460
Phe Ala Gln Gly Trp Gly Pro Ile Ser Tyr Ala Asn Gly Ser Gly Pro
465                 470                 475                 480
Asp Gln Arg Pro Tyr Cys Trp His Tyr Pro Lys Pro Cys Gly Ile
                485                 490                 495
Val Pro Ala Lys Ser Val Cys Gly Pro Val Tyr Cys Phe Thr Pro Ser
            500                 505                 510
Pro Val Val Gly Thr Thr Asp Arg Ser Gly Ala Pro Thr Tyr Asn
        515                 520                 525
Trp Gly Glu Asn Asp Thr Asp Val Phe Val Leu Asn Asn Thr Arg Pro
    530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Asp Ile Gly Gly Val Gly Asn
                565                 570                 575
Asn Thr Leu His Cys Pro Thr Asp Cys Phe Arg Lys His Pro Glu Ala
            580                 585                 590
Thr Tyr Ser Arg Cys Gly Ser Gly Pro Trp Ile Thr Pro Arg Cys Leu
        595                 600                 605
Val Asp Tyr Pro Tyr Arg Leu Trp His Tyr Pro Cys Thr Ile Asn Tyr
    610                 615                 620
Thr Ile Phe Lys Val Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Gln Trp
            660                 665                 670
Gln Val Leu Pro Cys Ser Phe Thr Thr Leu Pro Ala Leu Ser Thr Gly
        675                 680                 685
Leu Ile His Leu His Gln Asn Ile Val Asp Val Gln Tyr Leu Tyr Gly
    690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
            740                 745                 750
Ile Leu Asn Ala Ala Ser Leu Ala Gly Thr His Gly Leu Val Ser Phe
        755                 760                 765
```

```
Leu Val Phe Phe Cys Phe Ala Trp Tyr Leu Lys Gly Lys Trp Val Pro
770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
            835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Met
        915                 920                 925

Ala Gly Gly His Tyr Val Gln Met Ala Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Phe
            965                 970                 975

Ser Gln Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Arg
            995                 1000                1005

Glu Ile  Leu Leu Gly Pro Ala  Asp Gly Met Val Ser  Lys Gly Trp
1010                1015                1020

Arg Leu  Leu Ala Pro Ile Thr  Ala Tyr Ala Gln Gln  Thr Arg Gly
1025                1030                1035

Leu Leu  Gly Cys Ile Ile Thr  Ser Leu Thr Gly Arg  Asp Lys Asn
1040                1045                1050

Gln Val  Glu Gly Glu Val Gln  Ile Val Ser Thr Ala  Ala Gln Thr
1055                1060                1065

Phe Leu  Ala Thr Cys Ile Asn  Gly Val Cys Trp Thr  Val Tyr His
1070                1075                1080

Gly Ala  Gly Thr Arg Thr Ile  Ala Ser Pro Lys Gly  Pro Val Ile
1085                1090                1095

Gln Met  Tyr Thr Asn Val Asp  Lys Asp Leu Val Gly  Trp Pro Ala
1100                1105                1110

Pro Gln  Gly Ala Arg Ser Leu  Thr Pro Cys Thr Cys  Gly Ser Ser
1115                1120                1125

Asp Leu  Tyr Leu Val Thr Arg  His Ala Asp Val Ile  Pro Val Arg
1130                1135                1140

Arg Arg  Gly Asp Ser Arg Gly  Ser Leu Leu Ser Pro  Arg Pro Ile
1145                1150                1155

Ser Tyr  Leu Lys Gly Ser Ser  Gly Gly Pro Leu Leu  Cys Pro Ala
1160                1165                1170
```

```
-continued

Gly His Ala Val Gly Ile Phe Arg Ala Ala Val Cys Thr Arg Gly
    1175                1180                1185

Val Ala Lys Ala Val Asp Phe Ile Pro Val Glu Asn Leu Glu Thr
    1190                1195                1200

Thr Met Arg Ser Pro Val Phe Thr Asp Asn Ser Pro Pro Ala
    1205                1210                1215

Val Pro Gln Ser Phe Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Met Ser Lys Ala His Gly Ile Asp Pro Asn Ile
    1265                1270                1275

Arg Thr Gly Val Arg Thr Ile Thr Thr Gly Ser Pro Ile Thr Tyr
    1280                1285                1290

Ser Thr Tyr Gly Lys Phe Leu Ala Asp Gly Gly Cys Ser Gly Gly
    1295                1300                1305

Ala Tyr Asp Ile Ile Ile Cys Asp Glu Cys His Ser Thr Asp Ala
    1310                1315                1320

Thr Ser Ile Leu Gly Ile Gly Thr Val Leu Asp Gln Ala Glu Thr
    1325                1330                1335

Ala Gly Ala Arg Leu Val Val Leu Ala Thr Ala Thr Pro Pro Gly
    1340                1345                1350

Ser Val Thr Val Pro His Pro Asn Ile Glu Glu Val Ala Leu Ser
    1355                1360                1365

Thr Thr Gly Glu Ile Pro Phe Tyr Gly Lys Ala Ile Pro Leu Glu
    1370                1375                1380

Val Ile Lys Gly Gly Arg His Leu Ile Phe Cys His Ser Lys Lys
    1385                1390                1395

Lys Cys Asp Glu Leu Ala Ala Lys Leu Val Ala Leu Gly Ile Asn
    1400                1405                1410

Ala Val Ala Tyr Tyr Arg Gly Leu Asp Val Ser Val Ile Pro Thr
    1415                1420                1425

Ser Gly Asp Val Val Val Ala Thr Asp Ala Leu Met Thr Gly
    1430                1435                1440

Tyr Thr Gly Asp Phe Asp Ser Val Ile Asp Cys Asn Thr Cys Val
    1445                1450                1455

Thr Gln Thr Val Asp Phe Ser Leu Asp Pro Thr Phe Thr Ile Glu
    1460                1465                1470

Thr Thr Thr Leu Pro Gln Asp Ala Val Ser Arg Thr Gln Arg Arg
    1475                1480                1485

Gly Arg Thr Gly Arg Gly Lys Pro Gly Ile Tyr Arg Phe Val Ala
    1490                1495                1500

Pro Gly Glu Arg Pro Ser Gly Met Phe Asp Ser Ser Val Leu Cys
    1505                1510                1515

Glu Cys Tyr Asp Ala Gly Cys Ala Trp Tyr Glu Leu Thr Pro Ala
    1520                1525                1530

Glu Thr Thr Val Arg Leu Arg Ala Tyr Met Asn Thr Pro Gly Leu
    1535                1540                1545

Pro Val Cys Gln Asp His Leu Glu Phe Trp Glu Gly Val Phe Thr
    1550                1555                1560
```

-continued

Gly Leu Thr His Ile Asp Ala His Phe Leu Ser Gln Thr Lys Gln
1565                1570                1575

Ser Gly Glu Asn Phe Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Leu Thr
1625                1630                1635

His Pro Ile Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Val Val Leu Ser Gly Lys Pro Ala Ile Ile Pro Asp Arg
1685                1690                1695

Glu Val Leu Tyr Arg Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg Gln Ala
1730                1735                1740

Glu Val Ile Ala Pro Ala Val Gln Thr Asn Trp Gln Lys Leu Glu
1745                1750                1755

Thr Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Ser Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Ala Ile Leu Ser Ser Leu Thr Val
1940                1945                1950

```
Thr Gln Leu Leu Arg Arg Leu His Gln Trp Ile Ser Ser Glu Cys
1955                1960                1965

Thr Thr Pro Cys Ser Gly Ser Trp Leu Arg Asp Ile Trp Asp Trp
1970                1975                1980

Ile Cys Glu Val Leu Ser Asp Phe Lys Thr Trp Leu Lys Ala Lys
1985                1990                1995

Leu Met Pro Gln Leu Pro Gly Ile Pro Phe Val Ser Cys Gln Arg
2000                2005                2010

Gly Tyr Arg Gly Val Trp Arg Gly Asp Gly Ile Met His Thr Arg
2015                2020                2025

Cys His Cys Gly Ala Glu Ile Thr Gly His Val Lys Asn Gly Thr
2030                2035                2040

Met Arg Ile Val Gly Pro Arg Thr Cys Arg Asn Met Trp Ser Gly
2045                2050                2055

Thr Phe Pro Ile Asn Ala Tyr Thr Thr Gly Pro Cys Thr Pro Leu
2060                2065                2070

Pro Ala Pro Asn Tyr Lys Phe Ala Leu Trp Arg Val Ser Ala Glu
2075                2080                2085

Glu Tyr Val Glu Ile Arg Gln Val Gly Asp Phe His Tyr Val Thr
2090                2095                2100

Gly Met Thr Thr Asp Asn Leu Lys Cys Pro Cys Gln Val Pro Ser
2105                2110                2115

Pro Glu Phe Phe Thr Glu Leu Asp Gly Val Arg Leu His Arg Phe
2120                2125                2130

Ala Pro Pro Cys Lys Pro Leu Leu Arg Glu Glu Val Ser Phe Arg
2135                2140                2145

Val Gly Leu His Glu Tyr Pro Val Gly Ser Gln Leu Pro Cys Glu
2150                2155                2160

Pro Glu Pro Asp Val Ala Val Leu Thr Ser Met Leu Thr Asp Pro
2165                2170                2175

Ser His Ile Thr Ala Glu Ala Ala Gly Arg Arg Leu Ala Arg Gly
2180                2185                2190

Ser Pro Pro Ser Val Ala Ser Ser Ser Ala Ser Gln Leu Ser Ala
2195                2200                2205

Pro Ser Leu Lys Ala Thr Cys Thr Ala Asn His Asp Ser Pro Asp
2210                2215                2220

Ala Glu Leu Ile Glu Ala Asn Leu Leu Trp Arg Gln Glu Met Gly
2225                2230                2235

Gly Asn Ile Thr Arg Val Glu Ser Glu Asn Lys Val Val Ile Leu
2240                2245                2250

Asp Ser Phe Asp Pro Leu Val Ala Glu Glu Asp Glu Arg Glu Ile
2255                2260                2265

Ser Val Pro Ala Glu Ile Leu Arg Lys Ser Arg Arg Phe Ala Gln
2270                2275                2280

Ala Leu Pro Ile Trp Ala Arg Pro Asp Tyr Asn Pro Pro Leu Ile
2285                2290                2295

Glu Thr Trp Lys Lys Pro Asp Tyr Glu Pro Pro Val Val His Gly
2300                2305                2310

Cys Pro Leu Pro Pro Pro Gln Ser Pro Pro Val Pro Pro Pro Arg
2315                2320                2325

Lys Lys Arg Thr Val Val Leu Thr Glu Ser Thr Val Ser Thr Ala
2330                2335                2340
```

```
Leu Ala Glu Leu Ala Thr Lys Ser Phe Gly Ser Ser Ser Thr Ser
2345                2350                2355

Gly Ile Thr Gly Asp Asn Thr Thr Thr Ser Ser Glu Pro Ala Pro
2360                2365                2370

Ser Gly Cys Pro Pro Asp Ser Asp Ala Glu Ser Tyr Ser Ser Met
2375                2380                2385

Pro Pro Leu Glu Gly Glu Pro Gly Asp Pro Asp Leu Ser Asp Gly
2390                2395                2400

Ser Trp Ser Thr Val Ser Ser Glu Ala Asp Thr Glu Asp Val Val
2405                2410                2415

Cys Cys Ser Met Ser Tyr Ser Trp Thr Gly Ala Leu Val Thr Pro
2420                2425                2430

Cys Ala Ala Glu Glu Gln Lys Leu Pro Ile Asn Ala Leu Ser Asn
2435                2440                2445

Ser Leu Leu Arg His His Asn Leu Val Tyr Ser Thr Thr Ser Arg
2450                2455                2460

Ser Ala Cys Gln Arg Gln Lys Lys Val Thr Phe Asp Arg Leu Gln
2465                2470                2475

Val Leu Asp Ser His Tyr Gln Asp Val Leu Lys Glu Val Lys Ala
2480                2485                2490

Ala Ala Ser Lys Val Lys Ala Asn Leu Leu Ser Val Glu Glu Ala
2495                2500                2505

Cys Ser Leu Thr Pro Pro His Ser Ala Lys Ser Lys Phe Gly Tyr
2510                2515                2520

Gly Ala Lys Asp Val Arg Cys His Ala Arg Lys Ala Val Asn His
2525                2530                2535

Ile Asn Ser Val Trp Lys Asp Leu Leu Glu Asp Ser Val Thr Pro
2540                2545                2550

Ile Asp Thr Thr Ile Met Ala Lys Asn Glu Val Phe Cys Val Gln
2555                2560                2565

Pro Glu Lys Gly Gly Arg Lys Pro Ala Arg Leu Ile Val Phe Pro
2570                2575                2580

Asp Leu Gly Val Arg Val Cys Glu Lys Met Ala Leu Tyr Asp Val
2585                2590                2595

Val Ser Lys Leu Pro Leu Ala Val Met Gly Ser Ser Tyr Gly Phe
2600                2605                2610

Gln Tyr Ser Pro Gly Gln Arg Val Glu Phe Leu Val Gln Ala Trp
2615                2620                2625

Lys Ser Lys Lys Thr Pro Met Gly Phe Ser Tyr Asp Thr Arg Cys
2630                2635                2640

Phe Asp Ser Thr Val Thr Glu Ser Asp Ile Arg Thr Glu Glu Ala
2645                2650                2655

Ile Tyr Gln Cys Cys Asp Leu Asp Pro Gln Ala Arg Val Ala Ile
2660                2665                2670

Lys Ser Leu Thr Glu Arg Leu Tyr Val Gly Gly Pro Leu Thr Asn
2675                2680                2685

Ser Arg Gly Glu Asn Cys Gly Tyr Arg Arg Cys Arg Ala Ser Gly
2690                2695                2700

Val Leu Thr Thr Ser Cys Gly Asn Thr Leu Thr Cys Tyr Ile Lys
2705                2710                2715

Ala Arg Ala Ala Cys Arg Ala Ala Gly Leu Gln Asp Cys Thr Met
2720                2725                2730
```

| | | | | | | | | | |
|---|---|---|---|---|---|---|---|---|---|
| Leu | Val | Cys | Gly | Asp | Asp | Leu | Val | Val | Ile | Cys | Glu | Ser | Ala | Gly |
| | 2735 | | | | 2740 | | | | 2745 | | | | | |
| Val | Gln | Glu | Asp | Ala | Ala | Ser | Leu | Arg | Ala | Phe | Thr | Glu | Ala | Met |
| 2750 | | | | | 2755 | | | | | 2760 | | | | |
| Thr | Arg | Tyr | Ser | Ala | Pro | Pro | Gly | Asp | Pro | Pro | Gln | Pro | Glu | Tyr |
| 2765 | | | | | 2770 | | | | | 2775 | | | | |
| Asp | Leu | Glu | Leu | Ile | Thr | Ser | Cys | Ser | Ser | Asn | Val | Ser | Val | Ala |
| 2780 | | | | | 2785 | | | | | 2790 | | | | |
| His | Asp | Gly | Ala | Gly | Lys | Arg | Val | Tyr | Tyr | Leu | Thr | Arg | Asp | Pro |
| 2795 | | | | | 2800 | | | | | 2805 | | | | |
| Thr | Thr | Pro | Leu | Ala | Arg | Ala | Ala | Trp | Glu | Thr | Ala | Arg | His | Thr |
| 2810 | | | | | 2815 | | | | | 2820 | | | | |
| Pro | Val | Asn | Ser | Trp | Leu | Gly | Asn | Ile | Ile | Met | Phe | Ala | Pro | Thr |
| 2825 | | | | | 2830 | | | | | 2835 | | | | |
| Leu | Trp | Ala | Arg | Met | Ile | Leu | Met | Thr | His | Phe | Phe | Ser | Val | Leu |
| 2840 | | | | | 2845 | | | | | 2850 | | | | |
| Ile | Ala | Arg | Asp | Gln | Leu | Glu | Gln | Ala | Leu | Asp | Cys | Glu | Ile | Tyr |
| 2855 | | | | | 2860 | | | | | 2865 | | | | |
| Gly | Ala | Cys | Tyr | Ser | Ile | Glu | Pro | Leu | Asp | Leu | Pro | Pro | Ile | Ile |
| 2870 | | | | | 2875 | | | | | 2880 | | | | |
| Gln | Arg | Leu | His | Gly | Leu | Ser | Ala | Phe | Ser | Leu | His | Ser | Tyr | Ser |
| 2885 | | | | | 2890 | | | | | 2895 | | | | |
| Pro | Gly | Glu | Ile | Asn | Arg | Val | Ala | Ala | Cys | Leu | Arg | Lys | Leu | Gly |
| 2900 | | | | | 2905 | | | | | 2910 | | | | |
| Val | Pro | Pro | Leu | Arg | Ala | Trp | Arg | His | Arg | Ala | Arg | Ser | Val | Arg |
| 2915 | | | | | 2920 | | | | | 2925 | | | | |
| Ala | Arg | Leu | Leu | Ser | Arg | Gly | Gly | Arg | Ala | Ala | Ile | Cys | Gly | Lys |
| 2930 | | | | | 2935 | | | | | 2940 | | | | |
| Tyr | Leu | Phe | Asn | Trp | Ala | Val | Arg | Thr | Lys | Leu | Lys | Leu | Thr | Pro |
| 2945 | | | | | 2950 | | | | | 2955 | | | | |
| Ile | Ala | Ala | Ala | Gly | Arg | Leu | Asp | Leu | Ser | Gly | Trp | Phe | Thr | Ala |
| 2960 | | | | | 2965 | | | | | 2970 | | | | |
| Gly | Tyr | Ser | Gly | Gly | Asp | Ile | Tyr | His | Ser | Val | Ser | His | Ala | Arg |
| 2975 | | | | | 2980 | | | | | 2985 | | | | |
| Pro | Arg | Trp | Phe | Trp | Phe | Cys | Leu | Leu | Leu | Leu | Ala | Ala | Gly | Val |
| 2990 | | | | | 2995 | | | | | 3000 | | | | |
| Gly | Ile | Tyr | Leu | Leu | Pro | Asn | Arg | | | | | | | |
| 3005 | | | | | 3010 | | | | | | | | | |

<210> SEQ ID NO 7
<211> LENGTH: 9569
<212> TYPE: DNA
<213> ORGANISM: Artificial Sequence
<220> FEATURE:
<223> OTHER INFORMATION: synthetic sequence

<400> SEQUENCE: 7

```
gccagccccc gattgggggc gacactccac catagatcac tcccctgtga ggaactactg    60
tcttcacgca gaaagcgtct agccatggcg ttagtatgag tgtcgtgcag cctccaggac   120
cccccctccc gggagagcca tagtggtctg cggaaccggt gagtacaccg gaattgccag   180
gacgaccggg tcctttcttg gatcaacccg ctcaatgcct ggagatttgg gcgtgccccc   240
gcgagactgc tagccgagta gtgttgggtc gcgaaaggcc ttgtggtact gcctgatagg   300
gtgcttgcga gtgccccggg aggtctcgta gaccgtgcac catgagcacg aatcctaaac   360
```

```
ctcaaagaaa aaccaaacgt aacaccaacc gccgcccaca ggacgtcaag ttcccgggcg    420
gtggtcagat cgttggtgga gtttacctgt tgccgcgcag gggccccagg ttgggtgtgc    480
gcgcgactag gaagacttcc gagcggtcgc aacctcgtgg aaggcgacaa cctatcccca    540
aggctcgcca gcccgagggc agggcctggg ctcagcccgg gtaccttgg ccctctatg     600 gcaatgaggg catggggtgg gcaggatggc tcctgtcacc ccgcggctct cggcctagtt    660
ggggccccac ggaccccgg cgtaggtcgc gtaatttggg taaggtcatc gatacccctca   720 catgcggctt cgccgacctc atggggtaca ttccgctcgt cggcgccccc ctaggggcg    780 ctgccagggc cctggcgcat ggcgtccggg ttctggagga cggcgtgaac tatgcaacag   840
ggaatttgcc cggttgctct ttctctatct tcctcttggc tttgctgtcc tgtttgacca   900
tcccagcttc cgcttatgaa gtgcgcaacg tgtccggggt gtaccatgtc acgaacgact   960
gctccaactc aagcattgtg tatgaggcag cggacatgat catgcatacc cccgggtgcg  1020
tgccctgcgt tcgggagaac aactcctccc gctgctgggt agcgctcact cccacgctcg  1080
cggccaggaa cgccagcgtc cccactacga caatacgacg ccacgtcgat ttgctcgttg  1140
gggcggctgc tttctgctcc gctatgtacg tgggggatct ctgcggatct gttttccttg  1200
tctcccagct gttcaccttc tcgcctcgcc ggcatgagca agtacaggac tgcaattgct  1260
caatctatcc cggccacgta tcaggtcacc gcatggcttg ggatatgatg atgaactggt  1320
cacctacaac agccctagtg gtatcgcagt tactccggat cccacaagct gtcgtggaca  1380
tggtggcggg ggcccactgg ggagtcctgg cgggccttgc ctactattcc atggtgggga  1440
actgggctaa ggttttgatt gtgatgctac tctttgccgg cgttgacggg aacacccacg  1500
tgacaggggg gacgacagcc cgcaccaccc acggatttac gtccctcttt acacctgggc  1560
cgtctcagaa aatccagctt ataaacacca acggcagctg gcacatcaac aggactgccc  1620
tgaactgcaa tgactccctc caaactgggt tccttgccgc gctgttctac acacacaagt  1680
tcaactcgtc cggatgccca gagcgcatgg ccagctgccg ctccattgac aagttcgctc  1740 agggggtgggg tcccatcact tacgctgagc ctaacagctc ggaccagagg ccctattgct  1800
ggcactacgc gcctcgaccg tgtggtattg tacccgcgtc gcaggtgtgt ggtccagtgt  1860
attgcttcac cccaagccct gttgtggtgg ggacgaccga tcgtttcggc gtccctacgt  1920
atagctgggg ggagaatgag acggacgtgc tgcttctcaa caacgcgcgg ccgccgcaag  1980
gcaactggtt cggctgtaca tggatgaata gcactgggtt caccaagacg tgcggggccc  2040
ccccgtgtaa catcgggggg gtcggcaaca acaccttgac ctgccccacg gactgcttcc  2100
ggaagcaccc cgaggccact tacaccaaat gtggttcggg gccttggttg acacctaggt  2160
gcatggttga ctaccatac aggctttggc actaccctg cactgtcaac tttaccatct   2220
tcaaggttag gatgtatgtg gggggcgtgg agcacaggct caacgccgca tgcaattgga  2280
ctcgaggaga gcgttgtgac ttggaggaca gggatagatc agagcttagc ccgctgctgc  2340
tgtctacaac agagtggcag atactgccct gttccttcac caccctaccg gctctgtcca  2400
ctggtttgat ccatctccat cagaacatcg tggacgtgca atacctgtac ggtatagggt  2460
cagcggttgt ctccttttgca atcaaatggg agtatgtcct gttgctcttc cttctcctgg  2520
cggacgcgcg cgtctgtgcc tgcttgtgga tgatgctgct gatagctcag gctgaggccg  2580
ccttagagaa cctggtggtc ctcaatgcgg cgtccgtggc cggagcgcat ggcattctct  2640
ccttccttgt gttcttctgt gctgcctggt acatcaaggg caggctggtc cctggggcgg  2700
catatgcttt ctatggcgta tggccgctgc tcctgctcct gctggcgtta ccaccacgag  2760
```

```
catacgccat ggaccgggag atggctgcat cgtgcggagg cgcggttttc gtaggtctgg    2820
tactcttgac cttgtcacca cactataaag tgttcctcgc taggctcata tggtggttac    2880
aatattttat caccagagcc gaggcgcatt tgcaagtgtg ggtccccccc ctcaacgttc    2940 ggggggccg cgatgccatc atcctcctca cgtgcgcggt ccacccagag ctaatctttg    3000
acatcaccaa aatcttgctc gccatactcg gtccgctcat ggtgctccag gctggcataa    3060
ctagagtgcc gtacttcgtg cgcgctcaag ggctcattcg tgcatgcatg ttggtgcgga    3120
aagtcgctgg gggtcattat gtccaaatgg ctttcatgaa gctggccgca ctgacaggta    3180
cgtacgttta tgaccatctt actccactgc gggactgggc ccacgcgggc ctacgagacc    3240
ttgcggtggc agttgagccc gtcgtcttct ctgacatgga gaccaagatc atcacctggg    3300
gggcagacac cgcggcgtgt ggggacatca tcttgggtct acccgtctcc gcccgaaggg    3360
ggagggagat acttctggga ccggccgata gtcttgaagg gcaggggtgg cgactccttg    3420
cgcctatcac ggcctactcc aacagacgc ggggcctact tggctgcatc atcactagcc    3480
tcacaggccg gacaagaac caggtcgagg gggaggttca agtggtttcc accgcaacac    3540
aatctttcct ggcgacctgc gtcaacggcg tgtgttggac tgtctaccat ggcgccggct    3600
caaagaccct agccggccca aagggcccaa tcacccaaat gtacaccaat gtagaccagg    3660
acctcgtcgg ctggcaggcg cccccccgggg cgcgttcctt gacaccatgc acctgcggca    3720
gctcggacct ttacttggtc acgaggcatg ctgatgtcat tccggtgcgc cggcggggcg    3780
acagcagggg gagcctactc tcccccaggc ccgtctccta cttgaagggc tcttcgggtg    3840
gtccactgct ctgcccctcg gggcacgctg tgggcatctt ccgggctgct gtgtgcaccc    3900
ggggggttgc gaaggcggtg gactttgtac ccgttgagtc tatggaaact actatgcggt    3960
ccccggtctt cacggacaac tcgtccccc cggccgtacc gcagacattc caagtggccc    4020
atctacacgc tcccactggc agcggcaaga gcactaaggt gccggctgca tatgcagccc    4080
aagggtacaa ggtactcgtc ctgaacccgt ccgttgccgc caccttaggt tttgggcgt    4140 atatgtctaa ggcacatggt gtcgacccta acatcagaac tggggtaagg accatcacca    4200
cgggcgcccc catcacgtac tccacctatg caagttcct tgccgacggt ggttgctctg    4260
ggggcgccta tgacatcata atatgtgatg agtgccactc aactgactcg actaccatct    4320
tgggcatcgg cacagtcctg gaccaagcgg agacggctgg agcgcgactc gtcgtgctcg    4380
ccaccgctac gcctccggga tcggtcaccg tgccacatcc caatatcgag gaggtggccc    4440
tgtccaacac tggagagatc cccttctatg gcaaagccat ccccatcgag accatcaagg    4500
gggggaggca tctcatttc tgccattcca agaagaaatg tgacgagctc gccgcaaagc    4560
tgtcaggcct cggactcaat gctgtagcgt attaccgggg tcttgatgtg tccgtcatac    4620
cgaccagcgg agacgtcgtt gtcgtggcaa cagacgctct aatgacgggc tttaccggcg    4680
actttgactc agtgatcgac tgtaatacat gtgtcaccca gacagtcgat ttcagcttgg    4740
accctacctt caccattgag acgacgaccg tgccccaaga cgcggtgtcg cgctcgcagc    4800
ggcgaggcag gactggtagg ggcaggagag gcatctacag gtttgtgact ccaggagaac    4860
ggccctcggg catgttcgat tcctcggtcc tgtgtgagtg ctatgacgcg ggctgtgctt    4920
ggtacgagct cacgcccgcc gagacctcag ttaggttgcg ggcttaccta aatacaccag    4980
ggttgcccgt ctgccaggac catctggagt tctgggagag cgtcttcaca ggcctcaccc    5040
acatagatgc ccacttcttg tcccagacta agcaggcagg agacaacttc ccctacctgg    5100
tagcatacca ggctacagtg tgcgccaggg ctcaggctcc acctccatcg tgggatcaaa    5160
```

```
tgtggaagtg tctcatacgg ctaaagccta cgctgcacgg gccaacaccc ctgctgtata    5220
ggctaggagc cgtccaaaac gaggtcaccc tcacacaccc cataaccaaa tacatcatgg    5280
catgcatgtc ggctgacctg gaggtcgtca cgagcacctg ggtgctggta ggcggagtcc    5340
ttgcagctct ggccgcgtat tgcctgacaa caggcagcgt ggtcattgtg ggcaggatca    5400
tcttgtccgg gaagccggct atcattcccg acagggaagt cctctaccag gagttcgatg    5460
agatggaaga gtgcgcctca cacctcccctt acatcgaaca gggaatgcag ctcgccgagc    5520
aattcaagca gaaggcgctc gggttgctgc aaacagccac caagcaagcg gaggctgctg    5580
ctcccgtggt ggagtccaag tggcgagccc ttgagacctt ctgggcgaag cacatgtgga    5640
atttcatcag cgggatacag tacttagcag gcttgtccac tctgcctggg aaccccgcaa    5700
tagcatcact gatggcattc acagcctcta tcaccagccc gctcaccacc caacataccc    5760
tcctgtttaa catcttgggg ggatgggtgg ccgcccaact cgctcccccc agcgctgctt    5820
cggctttcgt gggcgccggc atcgctggtg cggctgttgg cagcataggc cttgggaagg    5880
tgcttgtgga catcctggcg ggttatggag caggggtggc aggcgcactc gtggccttta    5940
aggtcatgag cggcgagatg ccctccaccg aggacctggt caacttactc cctgccatcc    6000
tctctcctgg tgccctggtc gtcggggtcg tgtgcgcagc aatactgcgt cggcatgtgg    6060
gcccaggaga gggggctgtg cagtggatga accggctgat agcgttcgct tcgcggggta    6120
accacgtctc ccccacgcac tatgtgcctg agagcgacgc cgcagcgcgt gtcactcaga    6180
tcctctccag ccttaccatc actcagctgt tgaagaggct ccaccagtgg attaatgagg    6240
actgctccac gccatgctcc ggctcgtggc taagggatgt ttgggactgg atatgcacgg    6300
tgttgactga tttcaagacc tggctccagt ccaagctcct gccgcggtta ccgggagtcc    6360
ctttcctctc atgtcaacgt gggtacaagg gagtctggcg gggagacggc atcatgcaaa    6420
ccacctgccc atgtgagcca cagatcaccg gacatgtcaa aaacggttcc atgaggatcg    6480
ttgggcctaa aacctgcagc aacacgtggc atggaacatt ccccatcaac gcatacacca    6540
cgggcccctg cacaccctcc ccggcgccaa actattccag ggcgctgtgg cgggtggctg    6600
ctgaggagta cgtggaggtt acgcgggtgg gggatttcca ctacgtgacg ggcatgacca    6660
ctgacaacgt aaagtgccca tgccaggttc cggcccccga attcttcaca gaagtggatg    6720
gggtgcggct gcacaggtac gctccggcgt gcaaacctct cctacgggag gaggtcacat    6780
tccaggtcgg gctcaaccaa tacctggttg ggtcacagct cccatgtgag cccgaaccgg    6840
atgtagcagt gctcacttcc atgctcaccg accctccca cattacagca gagacggcta    6900
agcgtaggct ggcagggggg tctccccccct ccttggccag ctcttcagct agccagttgt    6960
ctgcgccttc cttgaaggcg acatgcacta cccgtcatga ctccccagac gctgacctca    7020
tcgaggccaa cctcctgtgg cggcaggaga tgggcgggaa catcacccgc gtggagtcag    7080
agaataaggt agtaattctg gactctttcg acccgcttcg agcggaggag gatgagagggg    7140 aagtatccgt tccggcggag atcctgcgga atccaggaa attccccccca gcgatgccca    7200 tatgggcacg cccggattac aaccctccac tgctagagtc ctggaaggac ccggactacg    7260
tccctccggt ggtacacggg tgcccattgc cacctaccaa ggcccctcca ataccacctc    7320
cacggagaaa gaggacggtt gtcctgacag aatccaccgt gtcttctgcc ttggcggagc    7380
tcgctacaaa gaccttcggc agctccgaat cgtcggccgt cgacagcggc acggcgaccc    7440
cccctcctga ccagccctcc gacgacggcg acacaggatc cgacgttgag tcgtactcct    7500
```

| | |
|---|---|
| ccatgccccc ccttgagggg gagccggggg accccgatct cagcgacggg tcttggtcta | 7560 |
| ccgtgagcga ggaggctagt gaggacgtcg tctgctgctc gatgtcctac acatggacag | 7620 |
| gcgccctgat cacgccatgc gccgcggagg aaagcaagct gcccatcaat gcgttgagca | 7680 |
| actctttgct gcgtcaccac aacatggtct atgccacaac atcccgcagc gcaagccagc | 7740 |
| ggcagaagaa ggtcaccttt gacagactgc aagtcctgga cgaccactac cgggacgtgc | 7800 |
| tcaaggagat gaaggcgaag gcgtccacag ttaaggctaa acttctatcc gtagaagaag | 7860 |
| cctgcaagct gacgccccca cattcggcca gatccaaatt tggctatggg gcaaaggacg | 7920 |
| tccggaacct atccagcaag gccgttaacc acatccgctc cgtgtggaag gacttgctgg | 7980 |
| aagacactga gacaccaatt gacaccacca tcatggcaaa aaatgaggtt ttctgcgtcc | 8040 |
| aaccagagaa aggaggccgc aagccagctc gccttatcgt attcccagac ttggggttc | 8100 |
| gtgtgtgcga gaaatggcc ctttacgacg tggtctccac ccttcctcag gccgtgatgg | 8160 |
| gctcctcata cggattccag tactctcctg gacagcgggt cgagttcctg gtgaatgcct | 8220 |
| ggaaatcaaa gaaaaaccct atgggcttcg catatgacac ccgctgtttt gactcaacgg | 8280 |
| tcactgagaa tgacatccgt gttgaggagt caatttacca atgttgtgac ttggcccccg | 8340 |
| aagccagaca ggccataaag tcgctcacag agcggcttta tatcgggggt cccctgacta | 8400 |
| attcaaaagg gcagaactgc ggttatcgcc ggtgccgcgc gagcggcgtg ctgacgacta | 8460 |
| gctgcgtaa taccctcaca tgttacttga aggcctctgc agcctgtcga gctgcaaagc | 8520 |
| tccaggactg cacgatgctc gtgtgcggag acgaccttgt cgttatctgt gaaagcgcgg | 8580 |
| gaacccaaga ggacgcggcg agcctacgag tcttcacgga ggctatgact aggtactctg | 8640 |
| ccccccccgg ggacccgccc caaccagaat acgacttgga gttgataaca tcatgctcct | 8700 |
| ccaatgtgtc ggtcgcgcac gatgcatctg gcaaagggt gtactacctc acccgtgacc | 8760 |
| ccaccacccc ccttgcgcgg gctgcgtggg agacagctag acacactcca gttaactcct | 8820 |
| ggctaggcaa catcatcatg tatgcgccca ccttatgggc aaggatgatt ctgatgactc | 8880 |
| acttcttctc catccttcta gctcaggagc aacttgaaaa agccctagat tgtcagatct | 8940 |
| acggggcctt ttactccatt gagccacttg acctacctca gatcattcaa cgactccatg | 9000 |
| gtcttagcgc attttcactc catagttact ctccaggtga gatcaatagg gtggcttcat | 9060 |
| gcctcaggaa acttgggta ccacccttgc gagtctggag acatcgggcc agaagtgtcc | 9120 |
| gcgctaagct actgtcccag gggggaggg ccgccacttg tggcaagtac ctcttcaact | 9180 |
| gggcagtaag gaccaagctc aaactcactc caatcccggc tgcgtcccag ttggacttgt | 9240 |
| ccggctggtt cgttgctggt tacagcgggg gagacatata tcacagcctg tctcgtgccc | 9300 |
| gaccccgctg gttcatgttg tgcctactcc tactttctgt aggggtaggc atctacctgc | 9360 |
| tccccaaccg atgaacgggg agctaaacac tccaggccaa taggccattt cctgtttttt | 9420 |
| tttttttttt ttttttttt tttccttttt ttcttttttt ttcttttctt tggtggctcc | 9480 |
| atcttagccc tagtcacggc tagctgtgaa aggtccgtga gccgcatgac tgcagagagt | 9540 |
| gctgatactg gcctctctgc agatcatgt | 9569 |

<210> SEQ ID NO 8
<211> LENGTH: 3010
<212> TYPE: PRT
<213> ORGANISM: Artificial Sequence
<220> FEATURE:
<223> OTHER INFORMATION: synthetic sequence

<400> SEQUENCE: 8

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Gly Pro Arg Leu Gly Val Arg Ala
                35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65              70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Val Tyr His Val Thr Asn Asp Cys Ser
                195                 200                 205

Asn Ser Ser Ile Val Tyr Glu Ala Ala Asp Met Ile Met His Thr Pro
210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Phe Cys
                260                 265                 270

Ser Ala Met Tyr Val Gly Asp Leu Cys Gly Ser Val Phe Leu Val Ser
                275                 280                 285

Gln Leu Phe Thr Phe Ser Pro Arg Arg His Glu Thr Val Gln Asp Cys
                290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Val Gly Asn Trp
                355                 360                 365

Ala Lys Val Leu Ile Val Met Leu Leu Phe Ala Gly Val Asp Gly Asn
                370                 375                 380

Thr His Val Thr Gly Gly Thr Thr Ala Arg Thr Thr His Gly Phe Thr
385                 390                 395                 400

Ser Leu Phe Thr Pro Gly Pro Ser Gln Lys Ile Gln Leu Ile Asn Thr
                405                 410                 415
```

-continued

```
Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Thr His Lys Phe Asn
        435                 440                 445

Ser Ser Gly Cys Pro Glu Arg Met Ala Ser Cys Arg Ser Ile Asp Lys
450                 455                 460

Phe Ala Gln Gly Trp Gly Pro Ile Thr Tyr Ala Glu Pro Asn Ser Ser
465                 470                 475                 480

Asp Gln Arg Pro Tyr Cys Trp His Tyr Ala Pro Arg Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Val Pro Thr Tyr Ser
        515                 520                 525

Trp Gly Glu Asn Glu Thr Asp Val Leu Leu Leu Asn Asn Thr Arg Pro
530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Phe
610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
690                 695                 700

Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Val Leu Asn Ala Ala Ser Val Ala Gly Ala His Gly Ile Leu Ser Phe
        755                 760                 765

Leu Val Phe Phe Cys Ala Ala Trp Tyr Ile Lys Gly Arg Leu Val Pro
770                 775                 780

Gly Ala Ala Tyr Ala Phe Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
            820                 825                 830
```

-continued

```
Pro His Tyr Lys Val Phe Leu Ala Arg Leu Ile Trp Trp Leu Gln Tyr
            835                 840                 845
Phe Ile Thr Arg Ala Glu Ala His Leu Gln Val Trp Val Pro Pro Leu
        850                 855                 860
Asn Val Arg Gly Gly Arg Asp Ala Ile Ile Leu Leu Thr Cys Ala Val
865                 870                 875                 880
His Pro Glu Leu Ile Phe Asp Ile Thr Lys Ile Leu Leu Ala Ile Leu
                885                 890                 895
Gly Pro Leu Met Val Leu Gln Ala Gly Ile Thr Arg Val Pro Tyr Phe
            900                 905                 910
Val Arg Ala Gln Gly Leu Ile Arg Ala Cys Met Leu Val Arg Lys Val
        915                 920                 925
Ala Gly Gly His Tyr Val Gln Met Ala Phe Met Lys Leu Ala Ala Leu
    930                 935                 940
Thr Gly Thr Tyr Val Tyr Asp His Leu Thr Pro Leu Arg Asp Trp Ala
945                 950                 955                 960
His Ala Gly Leu Arg Asp Leu Ala Val Ala Val Glu Pro Val Val Phe
                965                 970                 975
Ser Asp Met Glu Thr Lys Ile Ile Thr Trp Gly Ala Asp Thr Ala Ala
            980                 985                 990
Cys Gly Asp Ile Ile Leu Gly Leu Pro Val Ser Ala Arg Arg Gly Arg
        995                 1000                1005
Glu Ile Leu Leu Gly Pro Ala Asp Ser Leu Glu Gly Gln Gly Trp
    1010                1015                1020
Arg Leu Leu Ala Pro Ile Thr Ala Tyr Ser Gln Gln Thr Arg Gly
    1025                1030                1035
Leu Leu Gly Cys Ile Ile Thr Ser Leu Thr Gly Arg Asp Lys Asn
    1040                1045                1050
Gln Val Glu Gly Glu Val Gln Val Val Ser Thr Ala Thr Gln Ser
    1055                1060                1065
Phe Leu Ala Thr Cys Val Asn Gly Val Cys Trp Thr Val Tyr His
    1070                1075                1080
Gly Ala Gly Ser Lys Thr Leu Ala Gly Pro Lys Gly Pro Ile Thr
    1085                1090                1095
Gln Met Tyr Thr Asn Val Asp Gln Asp Leu Val Gly Trp Gln Ala
    1100                1105                1110
Pro Pro Gly Ala Arg Ser Leu Thr Pro Cys Thr Cys Gly Ser Ser
    1115                1120                1125
Asp Leu Tyr Leu Val Thr Arg His Ala Asp Val Ile Pro Val Arg
    1130                1135                1140
Arg Arg Gly Asp Ser Arg Gly Ser Leu Leu Ser Pro Arg Pro Val
    1145                1150                1155
Ser Tyr Leu Lys Gly Ser Ser Gly Gly Pro Leu Leu Cys Pro Ser
    1160                1165                1170
Gly His Ala Val Gly Ile Phe Arg Ala Ala Val Cys Thr Arg Gly
    1175                1180                1185
Val Ala Lys Ala Val Asp Phe Val Pro Val Glu Ser Met Glu Thr
    1190                1195                1200
Thr Met Arg Ser Pro Val Phe Thr Asp Asn Ser Ser Pro Pro Ala
    1205                1210                1215
Val Pro Gln Thr Phe Gln Val Ala His Leu His Ala Pro Thr Gly
    1220                1225                1230
```

```
Ser Gly Lys Ser Thr Lys Val Pro Ala Ala Tyr Ala  Ala Gln Gly
    1235                1240                     1245

Tyr Lys Val Leu Val Leu Asn Pro Ser Val Ala Ala  Thr Leu Gly
    1250                1255                     1260

Phe Gly Ala Tyr Met Ser Lys Ala His Gly Val Asp  Pro Asn Ile
    1265                1270                     1275

Arg Thr Gly Val Arg Thr Ile Thr Thr Gly Ala Pro  Ile Thr Tyr
    1280                1285                     1290

Ser Thr Tyr Gly Lys Phe Leu Ala Asp Gly Gly Cys  Ser Gly Gly
    1295                1300                     1305

Ala Tyr Asp Ile Ile Ile Cys Asp Glu Cys His Ser  Thr Asp Ser
    1310                1315                     1320

Thr Thr Ile Leu Gly Ile Gly Thr Val Leu Asp Gln  Ala Glu Thr
    1325                1330                     1335

Ala Gly Ala Arg Leu Val Val Leu Ala Thr Ala Thr  Pro Pro Gly
    1340                1345                     1350

Ser Val Thr Val Pro His Pro Asn Ile Glu Glu Val  Ala Leu Ser
    1355                1360                     1365

Asn Thr Gly Glu Ile Pro Phe Tyr Gly Lys Ala Ile  Pro Ile Glu
    1370                1375                     1380

Thr Ile Lys Gly Gly Arg His Leu Ile Phe Cys His  Ser Lys Lys
    1385                1390                     1395

Lys Cys Asp Glu Leu Ala Ala Lys Leu Ser Gly Leu  Gly Leu Asn
    1400                1405                     1410

Ala Val Ala Tyr Tyr Arg Gly Leu Asp Val Ser Val  Ile Pro Thr
    1415                1420                     1425

Ser Gly Asp Val Val Val Val Ala Thr Asp Ala Leu  Met Thr Gly
    1430                1435                     1440

Phe Thr Gly Asp Phe Asp Ser Val Ile Asp Cys Asn  Thr Cys Val
    1445                1450                     1455

Thr Gln Thr Val Asp Phe Ser Leu Asp Pro Thr Phe  Thr Ile Glu
    1460                1465                     1470

Thr Thr Thr Val Pro Gln Asp Ala Val Ser Arg Ser  Gln Arg Arg
    1475                1480                     1485

Gly Arg Thr Gly Arg Gly Arg Arg Gly Ile Tyr Arg  Phe Val Thr
    1490                1495                     1500

Pro Gly Glu Arg Pro Ser Gly Met Phe Asp Ser Ser  Val Leu Cys
    1505                1510                     1515

Glu Cys Tyr Asp Ala Gly Cys Ala Trp Tyr Glu Leu  Thr Pro Ala
    1520                1525                     1530

Glu Thr Ser Val Arg Leu Arg Ala Tyr Leu Asn Thr  Pro Gly Leu
    1535                1540                     1545

Pro Val Cys Gln Asp His Leu Glu Phe Trp Glu Ser  Val Phe Thr
    1550                1555                     1560

Gly Leu Thr His Ile Asp Ala His Phe Leu Ser Gln  Thr Lys Gln
    1565                1570                     1575

Ala Gly Asp Asn Phe Pro Tyr Leu Val Ala Tyr Gln  Ala Thr Val
    1580                1585                     1590

Cys Ala Arg Ala Gln Ala Pro Pro Pro Ser Trp Asp  Gln Met Trp
    1595                1600                     1605

Lys Cys Leu Ile Arg Leu Lys Pro Thr Leu His Gly  Pro Thr Pro
    1610                1615                     1620
```

```
Leu Leu Tyr Arg Leu Gly Ala Val Gln Asn Glu Val Thr Leu Thr
1625                1630                1635

His Pro Ile Thr Lys Tyr Ile Met Ala Cys Met Ser Ala Asp Leu
1640                1645                1650

Glu Val Val Thr Ser Thr Trp Val Leu Val Gly Val Leu Ala
1655                1660                1665

Ala Leu Ala Ala Tyr Cys Leu Thr Thr Gly Ser Val Val Ile Val
1670                1675                1680

Gly Arg Ile Ile Leu Ser Gly Lys Pro Ala Ile Pro Asp Arg
1685                1690                1695

Glu Val Leu Tyr Gln Glu Phe Asp Glu Met Glu Glu Cys Ala Ser
1700                1705                1710

His Leu Pro Tyr Ile Glu Gln Gly Met Gln Leu Ala Glu Gln Phe
1715                1720                1725

Lys Gln Lys Ala Leu Gly Leu Leu Gln Thr Ala Thr Lys Gln Ala
1730                1735                1740

Glu Ala Ala Ala Pro Val Val Glu Ser Lys Trp Arg Ala Leu Glu
1745                1750                1755

Thr Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ser Ile Thr Ser Pro Leu Thr Thr
1790                1795                1800

Gln His Thr Leu Leu Phe Asn Ile Leu Gly Gly Trp Val Ala Ala
1805                1810                1815

Gln Leu Ala Pro Pro Ser Ala Ala Ser Ala Phe Val Gly Ala Gly
1820                1825                1830

Ile Ala Gly Ala Ala Val Gly Ser Ile Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Val Met Ser Gly Glu Met Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Gln Ile Leu Ser Ser Leu Thr Ile
1940                1945                1950

Thr Gln Leu Leu Lys Arg Leu His Gln Trp Ile Asn Glu Asp Cys
1955                1960                1965

Ser Thr Pro Cys Ser Gly Ser Trp Leu Arg Asp Val Trp Asp Trp
1970                1975                1980

Ile Cys Thr Val Leu Thr Asp Phe Lys Thr Trp Leu Gln Ser Lys
1985                1990                1995

Leu Leu Pro Arg Leu Pro Gly Val Pro Phe Leu Ser Cys Gln Arg
2000                2005                2010
```

-continued

```
Gly Tyr Lys Gly Val Trp Arg Gly Asp Gly Ile Met Gln Thr Thr
    2015                2020                2025

Cys Pro Cys Gly Ala Gln Ile Thr Gly His Val Lys Asn Gly Ser
    2030                2035                2040

Met Arg Ile Val Gly Pro Lys Thr Cys Ser Asn Thr Trp His Gly
    2045                2050                2055

Thr Phe Pro Ile Asn Ala Tyr Thr Thr Gly Pro Cys Thr Pro Ser
    2060                2065                2070

Pro Ala Pro Asn Tyr Ser Arg Ala Leu Trp Arg Val Ala Ala Glu
    2075                2080                2085

Glu Tyr Val Glu Val Thr Arg Val Gly Asp Phe His Tyr Val Thr
    2090                2095                2100

Gly Met Thr Thr Asp Asn Val Lys Cys Pro Cys Gln Val Pro Ala
    2105                2110                2115

Pro Glu Phe Phe Thr Glu Val Asp Gly Val Arg Leu His Arg Tyr
    2120                2125                2130

Ala Pro Ala Cys Lys Pro Leu Leu Arg Glu Glu Val Thr Phe Gln
    2135                2140                2145

Val Gly Leu Asn Gln Tyr Leu Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Thr Ala Lys Arg Arg Leu Ala Arg Gly
    2180                2185                2190

Ser Pro Pro Ser Leu Ala Ser Ser Ser Ala Ser Gln Leu Ser Ala
    2195                2200                2205

Pro Ser Leu Lys Ala Thr Cys Thr Thr Arg His Asp Ser Pro Asp
    2210                2215                2220

Ala Asp Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Asp Pro Leu Arg Ala Glu Glu Asp Glu Arg Glu Val
    2255                2260                2265

Ser Val Pro Ala Glu Ile Leu Arg Lys Ser Arg Lys Phe Pro Pro
    2270                2275                2280

Ala Met Pro Ile Trp Ala Arg Pro Asp Tyr Asn Pro Pro Leu Leu
    2285                2290                2295

Glu Ser Trp Lys Asp Pro Asp Tyr Val Pro Pro Val Val His Gly
    2300                2305                2310

Cys Pro Leu Pro Pro Thr Lys Ala Pro Pro Ile Pro Pro Pro Arg
    2315                2320                2325

Arg Lys Arg Thr Val Val Leu Thr Glu Ser Thr Val Ser Ser Ala
    2330                2335                2340

Leu Ala Glu Leu Ala Thr Lys Thr Phe Gly Ser Ser Glu Ser Ser
    2345                2350                2355

Ala Val Asp Ser Gly Thr Ala Thr Ala Pro Pro Asp Gln Pro Ser
    2360                2365                2370

Asp Asp Gly Asp Thr Gly Ser Asp Val Glu Ser Tyr Ser Ser Met
    2375                2380                2385

Pro Pro Leu Glu Gly Glu Pro Gly Asp Pro Asp Leu Ser Asp Gly
    2390                2395                2400
```

```
Ser Trp Ser Thr Val Ser Glu Glu Ala Ser Glu Asp Val Val Cys
    2405                2410                2415

Cys Ser Met Ser Tyr Thr Trp Thr Gly Ala Leu Ile Thr Pro Cys
    2420                2425                2430

Ala Ala Glu Glu Ser Lys Leu Pro Ile Asn Ala Leu Ser Asn Ser
    2435                2440                2445

Leu Leu Arg His His Asn Met Val Tyr Ala Thr Thr Ser Arg Ser
    2450                2455                2460

Ala Ser Gln Arg Gln Lys Lys Val Thr Phe Asp Arg Leu Gln Val
    2465                2470                2475

Leu Asp Asp His Tyr Arg Asp Val Leu Lys Glu Met Lys Ala Lys
    2480                2485                2490

Ala Ser Thr Val Lys Ala Lys Leu Leu Ser Val Glu Glu Ala Cys
    2495                2500                2505

Lys Leu Thr Pro Pro His Ser Ala Arg Ser Lys Phe Gly Tyr Gly
    2510                2515                2520

Ala Lys Asp Val Arg Asn Leu Ser Ser Lys Ala Val Asn His Ile
    2525                2530                2535

Arg Ser Val Trp Lys Asp Leu Leu Glu Asp Thr Glu Thr Pro Ile
    2540                2545                2550

Asp Thr Thr Ile Met Ala Lys Asn Glu Val Phe Cys Val Gln Pro
    2555                2560                2565

Glu Lys Gly Gly Arg Lys Pro Ala Arg Leu Ile Val Phe Pro Asp
    2570                2575                2580

Leu Gly Val Arg Val Cys Glu Lys Met Ala Leu Tyr Asp Val Val
    2585                2590                2595

Ser Thr Leu Pro Gln Ala Val Met Gly Ser Ser Tyr Gly Phe Gln
    2600                2605                2610

Tyr Ser Pro Gly Gln Arg Val Glu Phe Leu Val Asn Ala Trp Lys
    2615                2620                2625

Ser Lys Lys Asn Pro Met Gly Phe Ala Tyr Asp Thr Arg Cys Phe
    2630                2635                2640

Asp Ser Thr Val Thr Glu Asn Asp Ile Arg Val Glu Glu Ser Ile
    2645                2650                2655

Tyr Gln Cys Cys Asp Leu Ala Pro Glu Ala Arg Gln Ala Ile Lys
    2660                2665                2670

Ser Leu Thr Glu Arg Leu Tyr Ile Gly Gly Pro Leu Thr Asn Ser
    2675                2680                2685

Lys Gly Gln Asn Cys Gly Tyr Arg Arg Cys Arg Ala Ser Gly Val
    2690                2695                2700

Leu Thr Thr Ser Cys Gly Asn Thr Leu Thr Cys Tyr Leu Lys Ala
    2705                2710                2715

Ser Ala Ala Cys Arg Ala Ala Lys Leu Gln Asp Cys Thr Met Leu
    2720                2725                2730

Val Cys Gly Asp Asp Leu Val Val Ile Cys Glu Ser Ala Gly Thr
    2735                2740                2745

Gln Glu Asp Ala Ala Ser Leu Arg Val Phe Thr Glu Ala Met Thr
    2750                2755                2760

Arg Tyr Ser Ala Pro Pro Gly Asp Pro Pro Gln Pro Glu Tyr Asp
    2765                2770                2775

Leu Glu Leu Ile Thr Ser Cys Ser Ser Asn Val Ser Val Ala His
    2780                2785                2790
```

-continued

```
Asp Ala Ser Gly Lys Arg Val Tyr Tyr Leu Thr Arg Asp Pro Thr
    2795            2800                    2805

Thr Pro Leu Ala Arg Ala Ala Trp Glu Thr Ala Arg His Thr Pro
    2810            2815                    2820

Val Asn Ser Trp Leu Gly Asn Ile Ile Met Tyr Ala Pro Thr Leu
    2825            2830                    2835

Trp Ala Arg Met Ile Leu Met Thr His Phe Phe Ser Ile Leu Leu
    2840            2845                    2850

Ala Gln Glu Gln Leu Glu Lys Ala Leu Asp Cys Gln Ile Tyr Gly
    2855            2860                    2865

Ala Cys Tyr Ser Ile Glu Pro Leu Asp Leu Pro Gln Ile Ile Gln
    2870            2875                    2880

Arg Leu His Gly Leu Ser Ala Phe Ser Leu His Ser Tyr Ser Pro
    2885            2890                    2895

Gly Glu Ile Asn Arg Val Ala Ser Cys Leu Arg Lys Leu Gly Val
    2900            2905                    2910

Pro Pro Leu Arg Val Trp Arg His Arg Ala Arg Ser Val Arg Ala
    2915            2920                    2925

Lys Leu Leu Ser Gln Gly Gly Arg Ala Ala Thr Cys Gly Lys Tyr
    2930            2935                    2940

Leu Phe Asn Trp Ala Val Arg Thr Lys Leu Lys Leu Thr Pro Ile
    2945            2950                    2955

Pro Ala Ala Ser Gln Leu Asp Leu Ser Gly Trp Phe Val Ala Gly
    2960            2965                    2970

Tyr Ser Gly Gly Asp Ile Tyr His Ser Leu Ser Arg Ala Arg Pro
    2975            2980                    2985

Arg Trp Phe Met Leu Cys Leu Leu Leu Leu Ser Val Gly Val Gly
    2990            2995                    3000

Ile Tyr Leu Leu Pro Asn Arg
    3005            3010
```

SYNTHETIC HEPATITIS C POLYPEPTIDE AND METHODS OF MAKING AND USING SAME

REFERENCE TO RELATED APPLICATIONS

This application is a Divisional of U.S. patent application Ser. No. 14/114,808, filed Jan. 27, 2014, which is a 35 U.S.C. § 371 U.S. national entry of International Application PCT/US2012/036098, having an international filing date of May 2, 2012, which claims the benefit of U.S. Provisional Application No. 61/481,457 filed May 2, 2011, the content of each of the aforementioned applications is herein incorporated by reference in their entirety.

STATEMENT OF GOVERNMENTAL INTEREST

This invention was made with government support under grant no. DA024565, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on May 2, 2012, is named P11517-02_ST25.txt and is 118,119 bytes in size

BACKGROUND OF THE INVENTION

HCV is a small enveloped Flaviviridae family virus with a 9.6-kb single, positive-stranded RNA genome consisting of a 5' untranslated region (UTR), a large open reading frame encoding the virus-specific proteins, and a 3' UTR. The 5' UTR contains an internal ribosome entry site (IRES) that mediates translation of a single polyprotein of approximately 3000 amino acids. The polyprotein consists of structural proteins (core, E1, and E2) located in the N terminus, followed by p7 and nonstructural proteins (NS2, NS3, NS4A, NS4B, NS5A, and NS5B) encoded in the remainder.

While there is a recognized need for an effective HCV vaccine, selection of the viral strain to be used as an antigen has been arbitrary. Studies in humans and chimpanzees have shown that the host immune system is able to launch an effective response to HCV, and people who have cleared infection once are likely to do so again, though this effect is potentially attributable to host genetics. The genetic diversity of HCV, which is even greater than that of HIV, poses a great challenge to the development of an effective vaccine. Selection of an appropriate strain as a vaccine candidate is crucial since even a single amino acid substitution could reduce vaccine effectiveness by eliminating recognition by T cells specific for that epitope. Use of an ancestral or consensus sequence as a vaccine candidate has been proposed for HIV-1. Compared to a consensus sequence, a mosaic approach (including multiple variant sequences of individual epitopes) generated more vigorous T cell responses to HIV-1 epitopes. Mosaic candidates have recently been identified for HCV although their effectiveness is still unknown.

Hepatitis C virus (HCV) affects approximately 170 million people worldwide. Approximately 20-25% of patients with acute hepatitis C achieve spontaneous clearance of the virus but 75%-80% develop chronic infection. Approximately 20% of chronic hepatitis C patients develop cirrhosis and of these, 4% will develop hepatocellular carcinoma and 6% will develop end stage liver disease. There is no available HCV vaccine and commonly used interferon-based treatment is toxic, prolonged, expensive, not consistently successful, and not effective in the most advanced forms of disease.

As such, there still exists an unmet need for more effective tools for preparing antigens, antibodies and vaccines against HCV and related viruses.

SUMMARY OF THE INVENTION

In accordance with an embodiment, the present invention provides a nucleic acid molecule encoding the genome of a synthetic hepatitis C virus subtype 1a (Bole1a) comprising the nucleotide sequence of SEQ ID NO: 1, or the complement thereof.

In accordance with another embodiment, the present invention provides an isolated nucleic acid molecule that specifically hybridizes to the nucleotide sequence set forth in SEQ ID NO: 1 or to the complement thereof.

In accordance with a further embodiment, the present invention provides a pair of oligonucleotide primers for PCR, wherein the first primer is an isolated nucleic acid molecule between about 10 and about 30 nucleotides in length that specifically hybridizes to the nucleotide sequence set forth in SEQ ID NO: 1 and the second primer is an isolated nucleic acid molecule between about 10 and about 30 nucleotides in length that specifically hybridizes to the complement of the nucleotide sequence set forth in SEQ ID NO: 1.

In accordance with still another embodiment, the present invention provides an isolated polypeptide encoded by nucleic acid comprising a nucleotide sequence of SEQ ID NO: 1.

In accordance with yet a further embodiment, the present invention provides an isolated polypeptide having the amino acid sequence of SEQ ID NO: 2.

In accordance with an embodiment, the present invention provides a viral particle comprising a) the last 27 amino acids of the core sequence of SEQ ID NO: 1 followed by the amino acid sequences of the E1 and E2 regions, and b) a reporter element.

In accordance with another embodiment, the present invention provides a HCV antigen comprising a polynucleotide molecule encoding between 15 to 100 contiguous amino acids of the nucleotide sequence set forth in SEQ ID NO: 1.

In accordance with a further embodiment, the present invention provides an antibody, or antigen binding portion thereof, which specifically binds to the to the nucleic acid molecule having the nucleotide sequence set forth in SEQ ID NO: 1.

In accordance with still another embodiment, the present invention provides a method of testing a sample for the presence of HCV in the sample, the method comprising detecting the presence of a polypeptide in the sample that specifically binds to the antibody disclosed above.

In accordance with an embodiment, the present invention provides a method of treating a subject infected with HCV comprising administering to the subject, a pharmaceutical composition comprising an antigen as described above, in an amount sufficient to stimulate an immune response to the antigen in the subject, such that the immune response is sufficient to decrease the viral load of HCV in the subject.

BRIEF DESCRIPTION OF THE DRAWINGS

FIG. 2A is a diversity plot comparing mean pairwise non-synonymous (dN) and synonymous (dS) diversity among subtype 1a sequences ("subtype 1a") to mean pairwise distance between Bole1a and subtype 1a sequences, using sliding window size of 20 codons. For this comparison, the original dataset of 390 full-genome sequences was the source of polyprotein reference sequences.

DETAILED DESCRIPTION OF THE INVENTION

Figure 1A:
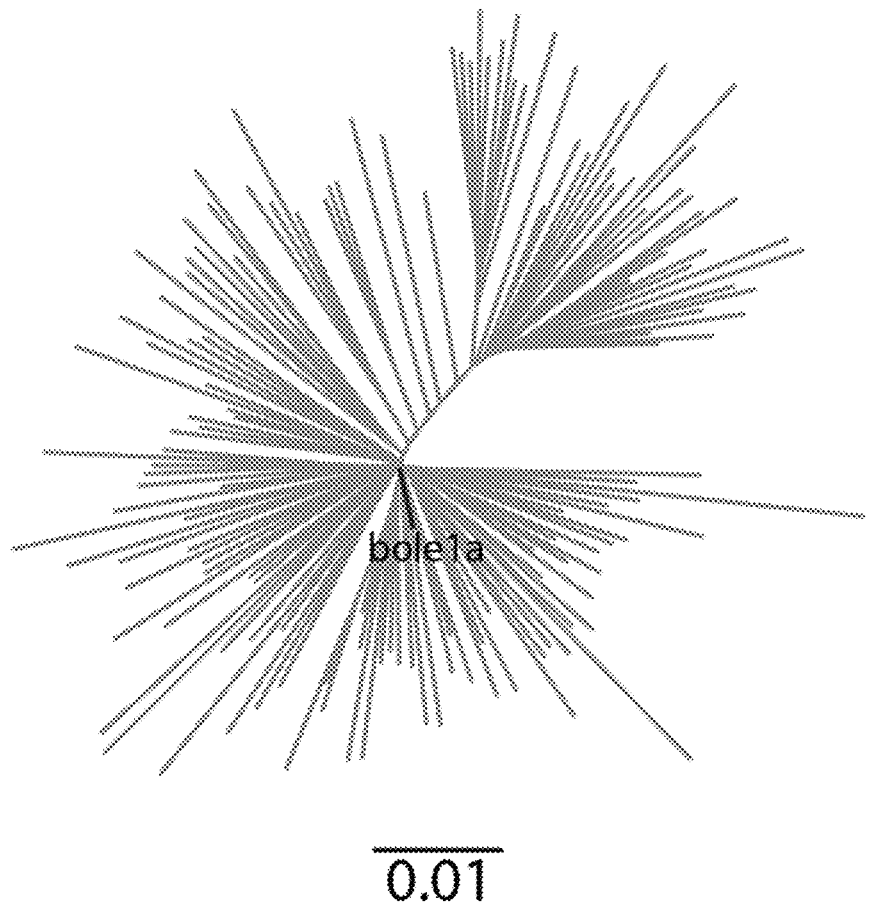
FIG. 1A-1B depict a neighbor-joining tree showing 1A Bole1a and the Yusim dataset 1B Bole1a and the E1E2 dataset. The Bole1a sequence is shown in bold in both figures.

The present invention provides a synthetic HCV subtype 1a genome (Bole1a) which is useful for vaccine research and development, antigen production, antibody production, diagnostic testing and oligonucleotide primer or probe production, and other uses.

In accordance with one or more embodiments, the present invention provides a synthetic subtype 1a HCV virus genome and the resulting computationally-derived genome is representative of widely circulating strains, has functional envelope genes that mediate entry into hepatoma cells in vitro, and matches more $CD8^+$ T cell epitopes than any other subtype 1a sequence in GenBank whether comparing all 9-mers or all known common epitopes.

In accordance with an embodiment, the present invention provides a nucleic acid molecule encoding the genome of a synthetic hepatitis C virus subtype 1a (Bole1a) comprising the nucleotide sequence of SEQ ID NO: 1, or the complement thereof.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al. (eds.), *Molecular Cloning, A Laboratory Manual*, $3^{rd}$ Edition, Cold Spring Harbor Laboratory Press, New York (2001) and Ausubel et al., *Current Protocols in Molecular Biology*, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence that encodes any of the Bole1a polypeptides, or proteins, or fragments or functional portions or functional variants thereof. For example, the nucleic acid can comprise a nucleotide sequence comprising SEQ ID NO: 1, or alternatively can comprise a nucleotide sequence that is degenerate to SEQ ID NO: 1.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein. In an embodiment, the present invention provides a nucleic acid molecule which is complementary to the full length nucleotide sequence of SEQ ID NO: 1.

As defined herein, a functional portion or functional variant of Bole1a polypeptides, or proteins, includes, for example, any of the core, E1, E2, NS3, NS4, NS5, and their subunits, UTR antigen proteins, and fragments thereof.

In an embodiment, the isolated nucleic acid molecule comprises a nucleotide sequence which is substantially the same as, e.g., has at least 50%, e.g., 60%, 70%, 80% or 90% or more, contiguous nucleic acid sequence identity to SEQ ID NO: 1, or the complement thereof.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, La Jolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech, Mountain View, Calif.). Examples of animal expression vectors include pEUK-C1, pMAM and pMAMneo (Clontech). Preferably, the recombinant expression vector is a viral vector, e.g., a retroviral vector, such as a lentiviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, lentiviruses and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA or RNA based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the Bole1a viral polypeptides, or proteins (including functional portions and functional variants thereof), such as core, E1, E2, NS3, NS4, NS5, UTR and the like, or to the nucleotide sequence which is complementary to or which hybridizes to the nucleotide sequence encoding the Bole1a viral polypeptides, or proteins or fragments thereof, as discussed above.

The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

In accordance with another embodiment, the present invention provides an isolated host cell comprising the isolated nucleic acid molecule comprising the nucleotide sequence of SEQ ID NO: 1, or the complement thereof.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant Bole1a virus, polypeptide, or protein, the host cell is preferably a mammalian cell. Most preferably, the host cell is a human cell. The host cell can be of any cell type, can originate from any type of tissue, and can be of any developmental stage. The host cell can be an liver cell, such as Hep3B cells for example.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a liver cell), which does not comprise any of the recombinant expression vectors, or a cell other than a skin cell, e.g., a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In accordance with a further embodiment, the host cell is a mammalian cell, preferably a liver cell or cell line derived therefrom.

In accordance with an embodiment, the present invention provides an isolated nucleic acid molecule that specifically hybridizes to the nucleotide sequence set forth in SEQ ID NO: 1 or to the complement thereof. In another embodiment, isolated nucleic acid molecule that specifically hybridizes to the nucleotide sequence set forth in SEQ ID NO: 1 or to the complement thereof comprises an oligonucleotide primer between about 10 and about 100 nucleotides in length, or various lengths of about 20, 30, 40, 50, 60, 70, 80 and about 90 nucleotides in length.

In accordance with an embodiment, the present invention provides an pair of oligonucleotide primers for PCR, wherein the first primer is an isolated nucleic acid molecule between about 10 and about 30 nucleotides in length that specifically hybridizes to the nucleotide sequence set forth in SEQ ID NO: 1 and the second primer is an isolated nucleic acid molecule between about 10 and about 30 nucleotides in length that specifically hybridizes to the complement of the nucleotide sequence set forth in SEQ ID NO: 1.

In accordance with an embodiment, the present invention provides an isolated polypeptide encoded by nucleic acid comprising the nucleotide sequence set forth in SEQ ID NO: 1, having the amino acid sequence of SEQ ID NO: 2.

In accordance with an embodiment, the present invention provides methods for constructing a synthetic viral genome polynucleotide sequences, including, for example, a series of synthetic HCV viral genome polynucleotide sequences, which can be used to construct viral particles, pseudoparticles, and fragments or portions of the polynucleotide sequences can be used for many purposes, including, for example, production of epitopes, antigens, antibodies and vaccines.

In one embodiment, the method for synthesizing a synthetic viral genome polynucleotide sequence generally comprises the following steps:

1. Select an appropriate number of representative non-recombinant genomic nucleotide sequences for the virus of interest and an appropriate number of outgroup sequences. For genomic regions lacking a representative sample, go to step 6.

2. Align sequences using an appropriate alignment program such as MUSCLE (Nucleic Acids Res. 32:1792-1797 (2004)) or ClustalX.

3. To avoid idiosyncrasies of any individual phylogeny, reconstruct 2 independent phylogenetic trees using a Bayesian or Maximum Likelihood method applied to two phylogenetically informative regions of the alignment. Run sufficient number of iterations to confirm convergence of parameters for phylogenetic trees.

4. Use both phylogenetic trees to infer ancestral sequences for the rest of the genome. The program used for estimation must infer the ancestral sequence as a probability distribution for each position, generating a probability for each base (e.g.: MrBayes or Garli).

5. Infer the final representative sequence in the following manner (methods I & II):

5a. For each nucleotide position i in the genome, if both trees agree on the maximum posterior probability (MPP) residue, the probability of that position pi is selected to be the greater of the two MPPs. These positions are defined as concordant.

5b. For each discordant position (where the MPP residue does not agree), either (method I) go to directly to step 5d or (method II) calculate the joint probability of the codon k containing the discordant position based on both trees. For concordant residues within such codons, the pi calculated in the previous step is used in calculating the joint probability.

5c. The codon with the higher joint MPP from the two trees is selected to represent that codon position. This codon-based analysis resolves cases where more than one position in the codon is discordant and accommodates 6-fold degenerate codons.

5d. To determine a stringent threshold for codon/nucleotide MPP, the inflection in the distribution of codon/nucleotide MPPs at which the variance in second derivative is less than 10-6 for MPP values is used as a threshold for resolving a codon/nucleotide. Each codon/nucleotide with an MPP greater than or equal to the threshold based on either tree is accepted as ancestral and its constituent positions are defined as resolved.

5e. Covariance analysis is used to examine still-unresolved positions. The basic assumption of phylogenetic reconstruction that each site evolves independently ignores covarying and interacting sites. In order to take such sites into consideration, the observed and expected frequencies of pairs of bases is determined and the chi-squared metric is calculated as shown in equation 1 and adjusted for multiple comparisons using the Holm-Bonferroni method at α=0.05.

$$\chi_{ij}2=(o_{ij}-e_{ij})/e_{ij} \qquad (1)$$

5f Using the adjusted chi-squared metric, all resolved positions j that significantly covaried with unresolved positions i are identified. In case of a positive interaction ($o_{ij}>e_{ij}$), the MPP codon/nucleotide containing the positively interacting residue is selected. For negative interactions ($o_{ij}<e_{ij}$), all codon/nucleotide with the negatively interacting base are eliminated and the MPP codon from the remaining is selected.

5g. At still-unresolved sites, the MPP codon is selected even if less than the threshold (this is rarely necessary).

5h. The result is the representative sequence.

6. (For genomic regions lacking a representative sequence sample) Using available sequences, determine the consensus sequence.

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means an enzyme or protein having structural, regulatory, or biochemical functions of a naturally occurring molecule.

In particular embodiments, a "functional variant" of an amino acid sequence as used herein, refers to no more than one, two, three, four, five, six, seven, eight, nine or ten amino acid substitutions in the sequence of interest. The functional variant retains at least one biological activity normally associated with that amino acid sequence. In particular embodiments, the functional variant retains at least about 40%, 50%, 60%, 75%, 85%, 90%, 95% or more biological activity normally associated with the full-length amino acid sequence. In other embodiments, a functional variant is an amino acid sequence that is at least about 60%, 70%, 80%, 90%, 95% 97% or 98% similar to the polypeptide sequence disclosed herein (or fragments thereof).

In accordance with an embodiment, the present invention provides an HCV pseudoviral particle comprising: a) the last 27 amino acids of the core sequence of SEQ ID NO: 1 followed by the amino acid sequences of the E1 and E2 regions; and b) a reporter element. In accordance with another embodiment, the pseudoviral particle comprises as a reporter element, the luciferase polyprotein or a functional portion thereof.

HIV readily forms pseudotypes or pseudoparticles with the envelope proteins of many different viruses. In particular, HIV pseudoparticles bearing native HCV E1 and E2 glycoproteins are infectious for the human hepatoma cell lines Huh-7 and PLC/PR5. Significantly, infectivity is pH-dependent and can be neutralized by a number of E2-specific mAbs. HCV pseudoviral particles can be generated by cotransfection of 293-T cells with equal amounts of expression plasmids expressing the viral gps or an empty vector and the envelope-defective pNL4.3.Luc.R$^-$E$^-$ proviral genome.

In accordance with an embodiment, the present invention provides a HCV antigen comprising a polynucleotide molecule encoding between 15 to 100 contiguous amino acids of the polypeptide encoded by the nucleotide sequence set forth in SEQ ID NO: 1, or a portion or fragment thereof. In another embodiment, the present invention provides a HCV antigen comprising the polypeptide having the amino acid sequence of SEQ ID NO: 2, or a portion or fragment thereof. In one or more further embodiments, the HCV antigen of the present invention comprises a polynucleotide molecule which encodes amino acids from the core, E1 and/or E2 regions of the polypeptide of SEQ ID NO: 2, or a portion or fragment thereof.

In accordance with an embodiment, the present invention provides a method of treating a subject infected with HCV comprising administering to the subject, a pharmaceutical composition comprising an antigen as described above, in an amount sufficient to stimulate an immune response to the antigen in the subject, such that the immune response is sufficient to decrease the viral load of HCV in the subject.

For purposes of the invention, the amount or dose of the vaccine compositions of the present invention that is administered should be sufficient to stimulate an immune response in the subject which will diminish the viral load of HCV in the subject over a reasonable time frame. The dose will be determined by the efficacy of the particular pharmaceutical formulation and the location of the target population of cells in the subject, as well as the body weight of the subject to be treated.

In another embodiment, the term "administering" means that at least one or more pharmaceutical compositions of the present invention are introduced into a subject, preferably a subject receiving treatment for a disease, and the at least one or more compositions are allowed to come in contact with the one or more disease related cells or population of cells having the target gene of interest in vivo.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In a further embodiment, the pharmaceutical compositions of the present invention can be used in combination with one or more additional therapeutically active agents which are known to be capable of treating conditions or diseases discussed above. For example, the described compositions of the present invention could be used in combination with one or more known therapeutically active agents, to treat a disease or condition such as HCV infection. Non-limiting examples of other therapeutically active agents that can be readily combined in a pharmaceutical composition of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In accordance with an embodiment, the present invention provides an antibody, or antigen binding portion thereof, which specifically binds to the nucleic acid molecule set forth in SEQ ID NO: 1, or a portion or fragment thereof, or the isolated polypeptide having the amino acid sequence of SEQ ID NO: 2, or a portion or fragment thereof.

The present invention provides monoclonal antibodies directed against the any of the HCV polypeptides, or proteins, including, for example, the core, E1 and/or E2, NS2, NS3, NS4, NS5 and their subunits, and fragments thereof. In an embodiment, the antibody is a human or humanized antibody molecule.

In accordance with yet another embodiment, the antibody is labeled with a detectable label.

Functional variants include, but are not limited to, derivatives that are substantially similar in primary structural sequence, but which contain e.g., in vitro or in vivo modifications, chemical and/or biochemical, that are not found in the parent binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like.

Nonlimiting examples of antibody fragments or antigen bindable fragments that bind to epitopes on the antigen include the following: Fab fragments, F(ab)$_2$ fragments, Fab' fragments, fragments produced by F(ab) expression libraries, F(ab')2 fragments, Fd fragments, Fd' fragments and Fv fragments. The antibodies may be human, or from animals other than humans, preferably mammals, such as rat, mouse, guinea pig, rabbit, goat, sheep, and pig. Preferred are mouse monoclonal antibodies and antigen-binding fragments or portions thereof. In addition, chimeric antibodies and hybrid antibodies are embraced by the present invention.

In an embodiment, the monoclonal antibody of the present invention can be obtained by culturing a hybridoma producing the antibody of the present invention in a culture medium, for example, a RPMI1640 medium that contains fetal bovine serum. Alternatively, it can be obtained by preparing a gene comprising a heavy chain or a light chain, in which a DNA encoding a constant region of heavy chain or light chain is ligated to a DNA encoding each variable region by means of a PCR method or a chemical synthesis; inserting the obtained gene into a conventionally-used expression vector (e.g., pcDNA3.1 (Invitrogen) capable of expressing the gene; expressing the gene in a host cell such as a CHO cell (Chinese hamster ovary cell) or *Escherichia coli* to produce the antibody; and purifying the obtained antibody from the culture medium using a Protein A/G column or the like.

Furthermore, the monoclonal antibody of the present invention may be obtained by: preparing a hybridoma from a mammal immunized with a recombinant fusion protein comprising any of the HCV proteins, or fragments thereof, including for example, core, E1, E2, NS2, NS3, NS4 and NS5 proteins and their subunits, and one or more other proteins; expressing the fusion protein in a bacterial culture; purifying the fusion protein from bacterial lysates; mixing the purified fusion protein comprising any of the HCV proteins, or fragments thereof, with adjuvant and inoculating the mammal with the purified fusion protein. The inoculated mammals are given a booster inoculation after three weeks and then the splenocytes and lymphocytes are collected three days after the booster. Lymphocytes and splenocytes were fused with murine B cell hybridoma cells, such as SP2/mIL6 cells (ATCC), and propagated using HFCS supplement (Roche) according to manufacturer's instructions. Hybridomas are then screened for reactivity with the various species of recombinant HCV proteins, or fragments thereof.

Included in the scope of the present invention are conjugates, e.g., bioconjugates, comprising any of the inventive monoclonal antibodies (including any of the functional portions or variants thereof), host cells, populations of host cells, or antibodies, or antigen binding portions thereof. Conjugates, as well as methods of synthesizing conjugates in general, are known in the art. See, for instance, Hudecz, F., Methods Mol. Biol., 298: 209-223 (2005) and Kirin et al., Inorg. Chem., 44(15): 5405-5415 (2005).

The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for any of the HCV polypeptides, or proteins, including, for example, core, E1, E2, NS2, NS3, NS4 and NS5 proteins and their subunits, and fragments thereof.

Methods of testing antibodies for the ability to bind any of the HCV proteins, or fragments thereof are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, Eur. J. Immunol., 5: 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, J. Immunol. Methods, 74(2): 361-67 (1984), and Roder et al., Methods Enzymol., 121: 140-67 (1986)), and bacteriophage vector expression systems (see, e.g., Huse et al., *Science*, 246: 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761. Humanized antibodies can also be generated using the antibody resurfacing technology described in U.S. Pat. No. 5,639,641 and Pedersen et al., J. Mol. Biol., 235: 959-973 (1994).

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7: 697-704 (1994)). Antibody fragments of the invention, however, are not limited to these exemplary types of antibody fragments.

In another embodiment, the antibody, or antigen binding fragment thereof, is modified to comprise a detectable label, such as, for instance, a radioisotope, a fluorophore (e.g., fluorescein isothiocyanate (FITC), phycoerythrin (PE)), an enzyme (e.g., luciferase, alkaline phosphatase, horseradish peroxidase), and element particles (e.g., gold or magnetic particles).

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, protein A/G immunoprecipitation chromatography, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The antibodies of the present invention can be employed to prepare antigen-antibody affinity columns, which may be used for the purification of the antigen. For example, gel supports or beads can be activated with various chemical compounds, e.g., cyanogen bromide, N-hydroxysuccinimide esters, and antibodies can be bound thereto. More particularly, and by way of example, antibodies can be added to Affigel-10 (BioRad, Hercules, Calif.), a gel support which is activated with N-hydroxysuccinimide esters, such that the antibodies form covalent linkages with the agarose gel bead support. The antibodies are then coupled to the gel via amide bonds with a spacer arm. The remaining activated esters are then quenched with ethanolamine HCl, 1 M, pH 8. The column is washed with water, followed by 0.23 M glycine HCl, pH 2.6, to remove any non-conjugated antibody or extraneous protein. The column is then equilibrated in phosphate buffered saline (PBS), pH 7.3, with appropriate detergent, and the sample materials, i.e., cell culture supernatants or cell extracts, for example, containing the cancer-specific antigens (e.g., prepared using appropriate membrane solubilizing surfactants) are slowly passed over the column. The column is washed with PBS/surfactant until the optical density falls to background. The protein is then eluted from the column with 0.23 M glycine-HCl, pH 2.6/surfactant. The purified antigens are then dialyzed against PBS/surfactant.

Methods of detecting the presence of HCV in a host and methods of treating or preventing infection of a host with HCV are further provided by the present invention. The inventive method of detecting the presence of HCV in a host comprises (i) contacting a sample comprising cells of the host with any of the inventive antibodies, or antigen binding fragments thereof, described herein, thereby forming a complex, and (ii) detecting the complex, wherein detection of the complex is indicative of the presence of HCV infection in the host.

In accordance with an embodiment, the present invention provides a method of testing a sample for the presence of HCV in the sample, the method comprising detecting the presence of a polypeptide in the sample that specifically binds to the antibody as described herein.

The present invention further provides a method for localizing cells infected with HCV in a subject, especially cells expressing the core, E1, E2, NS2, NS3, NS4 and NS5 proteins and their subunits, and fragments thereof, comprising: (a) administering to the subject a detectably-labeled monoclonal antibody of the invention, or binding fragment thereof; (b) allowing the detectably-labeled (e.g., radiolabeled; flurochrome labeled, or enzyme labeled, for example, via ELISA) monoclonal antibody, or binding fragment thereof, to bind to the infected cells within the subject; and (c) determining the location of the labeled monoclonal antibody or binding fragment thereof, within the subject.

In a further embodiment, the antibody of the invention may be labeled with a detectable moiety, such as a fluorophore, a chromophore, a radionuclide, a chemiluminescent agent, a bioluminescent agent and an enzyme.

In an embodiment, antibodies of the present invention are labeled with such reagents using protocols and techniques known and practiced in the art. See, for example, Wenzel and Meares, *Radioimmunoimaging and Radioimmunotherapy*, Elsevier, New York, (1983); Colcer et al., Meth. Enzymol., 121: 802-816 (1986); and *Monoclonal Antibodies for Cancer Detection and Therapy*, Baldwin et al., (eds) Academic Press, 303-316 (1985), for techniques relating to the radiolabeling of antibodies.

In an embodiment, the antibodies, or binding fragments thereof, are delivered parenterally, such as by intravenous, subcutaneous, or intraperitoneal administration, e.g., injection. Suitable buffers, carriers, and other components known in the art can be used in formulating a composition comprising the antibody or fragments for suitable shelf-life and compatibility for the administration. These substances may include ancillary agents such as buffering agents and protein stabilizing agents (e.g., polysaccharides).

More specifically, therapeutic formulations of the antibodies, or binding fragments thereof, are prepared for storage by mixing the antibodies or their binding fragments, having the desired degree of purity, with optional physiologically acceptable carriers, excipients, or stabilizers (*Remington's Pharmaceutical Sciences*, 17th edition, (Ed.) A. Osol, Mack Publishing Company, Easton, Pa., (1985)), in lyophilized form or in the form of aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (e.g., about 10-15 amino acid residues or less) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (polysorbates), PLURONICS™ (block copolymers of ethylene oxide (EO) and propylene oxide (PO)) or polyethylene glycol (PEG). The antibodies, or binding fragments thereof, also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

Antibodies or their binding fragments to be used for in vivo administration must be sterile. This is readily accomplished by filtration through sterile filtration membranes, prior to, or following lyophilization and reconstitution. The antibodies, or binding fragments thereof, ordinarily will be stored in lyophilized form or in solution.

Therapeutic antibody compositions generally are placed into a container having a sterile access port, for example, an intravenous solution bag or vial having a stopper pierceable by a hypodermic injection needle. The route of administration of the antibodies, or binding fragments thereof, in accordance with the present invention, is in accord with known methods, e.g., injection or infusion by intravenous, intraperitoneal, intramuscular, intraarterial, subcutaneous, intralesional routes, by aerosol or intranasal routes, or by sustained release systems as noted below. The antibodies, or binding fragments thereof, are administered continuously by infusion or by bolus injection. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res., 15: 167-277 (1981) and Langer, Chem. Tech., 12: 98-105 (1982)), or poly(vinylalcohol), polylactides (U.S. Pat. No. 3,773,919), copolymers of L-glutamic acid and gamma ethyl-L-glutamate (Sidman et al., Biopolymers, 22: 547-556 (1983)), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid (EP 133,988).

An effective amount of antibody to be employed therapeutically will depend, for example, upon the therapeutic and treatment objectives, the route of administration, the age, condition, and body mass of the patient undergoing treatment or therapy, and auxiliary or adjuvant therapies being provided to the patient. Accordingly, it will be necessary and routine for the practitioner to titer the dosage and modify the route of administration, as required, to obtain the optimal therapeutic effect. A typical daily dosage might range from about 1 mg/kg to up to about 100 mg/kg or more, preferably from about 0.1 to about 10 mg/kg/day depending on the above-mentioned factors. Typically, the clinician will administer antibody until a dosage is reached that achieves the desired effect. The progress of this therapy is easily monitored by conventional assays.

Various adjuvants may be used to increase the immunological response to the antigen or vaccine and to elicit specific antibodies according to the present invention. Depending on the host species to be immunized, adjuvants may include, but are not limited to, Freund's (complete and incomplete), mineral gels, such as aluminum hydroxide, surface active agents, such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

The antibodies of the present invention are also useful for in vitro diagnostic applications for the detection of HCV infected cells that possess the antigen for which the antibodies are specific. As detailed above, in vitro diagnostic methods include immunohistological or immunohistochemical detection of HCV infected cells (e.g., on human tissue, or on cells dissociated from excised specimens), or serological detection of HCV associated antigens (e.g., in blood samples or other biological fluids). Immunohistochemical techniques involve staining a biological specimen, such as a tissue specimen, with one or more of the antibodies of the invention and then detecting the presence on the specimen of antibody-antigen complexes comprising antibodies bound to the cognate antigen. The formation of such antibody-antigen complexes with the specimen indicates the presence of HCV infection in the tissue.

Detection of the antibody on the specimen can be accomplished using techniques known in the art such as immunoenzymatic techniques, e.g., immunoperoxidase staining technique, or the avidin-biotin technique, or immunofluorescence techniques (see, e.g., Ciocca et al., Meth. Enzymol., 121: 562-79 (1986), and *Introduction to Immunology*, ($2^{nd}$ Ed), 113-117, Macmillan Publishing Company (1986)). Serologic diagnostic techniques involve the detection and quantification of tumor-associated antigens that have been secreted or "shed" into the serum or other biological fluids of patients thought to be suffering from cancer, as mentioned above. Such antigens can be detected in the body fluids using techniques known in the art, such as radioimmunoassays (RIA) or enzyme-linked immunoabsorbant assays (ELISA), wherein antibody reactive with the shed antigen is used to detect the presence of the antigen in a fluid sample (See, e.g., Uotila et al., J. Immunol. Methods, 42: 11 (1981) and Fayed et al., Disease Markers, 14: 155-160 (1998)).

In an embodiment, the present invention provides a method of detection of circulating serum antibodies specific for HCV proteins in a biological sample from a subject using an ELISA assay comprising: (a) contacting said at least one biological sample having at least one antibody specific for HCV protein, or at least one fragment of said protein with an HCV protein or a fragment thereof, and (b) detecting the formation of an antigen-antibody complex between the HCV protein or a fragment thereof, and an HCV specific antibody or fragment thereof, present in the biological sample.

The antibody or antibodies which is/are used in the context of the present invention can, themselves, be linked to a detectable label. Such a detectable label allows for the presence of, or the amount of the primary immune complexes to be determined. Alternatively, the first added component that becomes bound within the primary immune complexes can be detected by means of a second binding ligand that has binding affinity for the first antibody. In these cases, the second binding ligand is itself, often an antibody, which can be termed a "secondary" antibody. The primary immune complexes are contacted with the labeled, secondary binding ligand, or antibody, for a period of time sufficient to allow the formation of secondary immune complexes. The secondary immune complexes are then washed to remove any non-specifically bound labeled secondary antibodies or ligands, and the remaining label in the secondary immune complexes is then detected.

In an embodiment a method of detecting the presence and extent of infection of HCV in a patient is provided, comprising: determining the level of the antigen in a sample of bodily fluid or a tissue section from the patient and correlating the quantity of the antigen with the presence and extent of the infection in the patient. In one embodiment, the antigen is detected by (1) adding monoclonal antibody specific for core, E1, E2, NS2, NS3, NS4 and NS5 proteins and their subunits, and fragments thereof to the sample or tissue section; (2) adding goat anti-mouse IgG antibody conjugated with peroxidase; (3) fixing with diaminobenzidene and peroxide, and (4) examining the sample or section, wherein reddish brown color indicates that the cells bear the antigen.

In another embodiment, the present invention provides a method of making affinity-purified polyclonal antibodies using a 10 kD recombinant version of the core, E1, E2, NS2, NS3, NS4 and NS5 proteins and their subunits, and fragments thereof. The common leader peptide is transfected into bacteria and the leader peptide is expressed and is suitably soluble in aqueous solution. Polyclonal antibodies are ordinarily obtained from the serum of goat or rabbit immunized with a particular antigen, in an embodiment, the antigen is the 10 kD recombinant version of the core, E1, E2, NS2, NS3, NS4 and NS5 proteins and their subunits, and fragments thereof. The antiserum is affinity purified to remove nonspecific antibodies, increasing sensitivity and reducing background. Further purification is performed to remove potential nonspecific reactivities among related animal species, or to reduce shared reactivity with other heavy and light chains. In an embodiment, the purified antibody is labeled with a detectable marker, for example, rhodamine. The purified polyclonal antibodies are used to detect antigen using tissue samples that are fixed and embedded in paraffin, using methods known in the art.

Further methods include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, for a period of time sufficient to allow the formation of immune complexes (tertiary immune complexes). The third ligand or antibody is linked to a detectable label, allowing detection of the tertiary immune complexes thus formed.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In an embodiment, the monoclonal antibodies, or binding fragments thereof, according to the present invention, are used to quantitatively or qualitatively detect the presence of the any of the HCV proteins, or fragments thereof, on or in various skin or other cells. This can be achieved, for example, by immunofluorescence techniques employing a fluorescently labeled antibody, coupled with light microscopic, flow cytometric, or fluorometric detection. In addition, the antibodies, or binding fragments thereof, according to the present invention may additionally be employed histologically, as in immunofluorescence, immunoelectron microscopy, or non-immuno assays, for in situ detection of the cancer-specific antigen on cells, such as for use in monitoring, diagnosing, or detection assays.

In yet another embodiment, in situ detection is accomplished by removing a histological specimen from a patient, and applying thereto a labeled antibody according to this invention. The antibody, or antigen-binding fragment thereof, is preferably applied by overlaying the labeled antibody or fragment onto the biological sample. Through the use of such a procedure, it is possible to determine not only the presence of the antigen, or conserved variants, or peptide fragments, but also its distribution in the examined tissue. Those of ordinary skill in the art will readily recognize that any of a wide variety of histological methods, e.g., staining procedures, can be modified in order to achieve such in situ detection.

In an immunoassay of the present invention, a biological sample may be brought into contact with, and immobilized onto, a solid phase support or carrier, such as nitrocellulose, or other solid support or matrix, which is capable of immobilizing cells, cell particles, membranes, or soluble proteins. The support is then washed with suitable buffers, followed by treatment with the detectably-labeled antibody. The solid phase support is then washed with buffer a second time to remove unbound antibody. The amount of bound label on the solid support is then detected by conventional means. Accordingly, in another embodiment of the present invention, compositions are provided comprising the monoclonal antibodies, or binding fragments thereof, bound to a solid phase support, such as described herein.

By solid phase support, or carrier, or matrix, is meant any support capable of binding an antigen or an antibody. Well-known supports or carriers include glass, plastic, nylon wool, polystyrene, polyethylene, polypropylene, dextran, nylon, amylases, films, resins, natural and modified celluloses, polyacrylamides, agarose, alumina gels, gabbros, and magnetite. The nature of the carrier can be either soluble to some extent, or insoluble for the purposes of the present invention. The support material may have virtually any possible structural configuration as long as the coupled molecule is capable of binding to an antigen or antibody. Thus, the support configuration may be spherical, as in a bead, cylindrical, as in the inside surface of a test tube, or the external surface of a rod. Alternatively, the surface may be flat, such as a sheet, film, test strip, stick, and the like.

In an embodiment, the solid support is inert to the reaction conditions for binding and may have reactive groups, or activated groups, in order to attach the monoclonal antibody, a binding fragment, or the binding partner of the antibody. The solid phase support can also be useful as a chromatographic support, such as the carbohydrate polymers SEPHAROSE™ (crosslinked agarose beads), SEPHADEX™ (crosslinked dextran gel), or agarose. Indeed, a large number of such supports for binding antibody or antigen are commercially available and known to those having skill in the art.

The binding activity for a given antibody may be determined by well-known methods. With respect to the cancer specific antibodies of the present invention, numerous ways to detectably label such protein molecules are known and practiced in the art. For example, in an embodiment, the antibodies can be detectably labeled is by linking the antibody to an enzyme, e.g., for use in an enzyme immunoassay (EIA), (Voller et al., Diagnostic Horizons, 2: 1-7 (1978); Butler et al., Meths. Enzymol., 73: 482-523 (1981)). The enzyme that is bound to the antibody reacts with an appropriate substrate, preferably a chromogenic substrate, so as to produce a chemical moiety which can be detected, for example, by spectrophotometric, fluorometric, or by visual detection means. Nonlimiting examples of enzymes which can be used to detectably label the antibodies include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, ribonuclease, urease, catalase, glucose-6-phosphate dehydrogenase, glucoamylase and acetylcholinesterase. The detection can be accomplished by chrommetric methods, which employ a chromogenic substrate for the enzyme, or by visual comparison of the extent of enzymatic reaction of a substrate compared with similarly prepared standards or controls.

The antibodies of the present invention, or their antigen-binding fragments can also be labeled using a fluorescent compound. When the fluorescently labeled antibody is exposed to light of the proper wavelength, its presence can then be detected due to fluorescence. Some of the most commonly used fluorescent labeling compounds include fluorescein isothiocyanate, rhodamine, phycoerythrin, phycocyanin, allophycocyanin, o-phthaldehyde and fluorescamine.

In an alternate embodiment, the antibodies of the present invention can also be detectably labeled by coupling them to a chemiluminescent compound. The presence of the chemiluminescent-tagged antibody is then determined by detecting the presence of luminescence that develops during the course of a chemical reaction. Examples of particularly useful chemiluminescent labeling compounds include, without limitation, luminol, isoluminol, theromatic acridinium ester, imidazole, acridinium salt and oxalate ester. Similarly, a bioluminescent compound may be used to label the antibodies of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent labeling compounds include luciferin, luciferase and aequorin.

The following examples further illustrate the invention but, of course, should not be construed as in any way limiting its scope.

EXAMPLES

Human subjects. The Baltimore Before and After Acute Study of Hepatitis (BBAASH) cohort is a prospective study of persons at risk for hepatitis C infection. Eligible participants have a history of or ongoing intravenous drug use and are seronegative for anti-HCV antibodies at enrollment. Written consent was obtained from each participant. Once enrolled, participants receive counseling to reduce intravenous drug use and its complications. Blood is drawn for isolation of serum, plasma, and peripheral blood mononuclear cells (PBMC) in a protocol designed for monthly follow-up. Participants with acute HCV infection were referred for evaluation of treatment. The study was approved by the Institutional Review Board at the Johns Hopkins School of Medicine.

Synthetic Coding Sequence Reconstruction. HCV subtype 1a (n=390) and 1b (n=296) sequences that included at least the entire open reading frame of the polyprotein, were obtained from human specimens, and were not epidemiologically redundant were downloaded from GenBank (accession numbers AB016785, AB049087-101, AB154177, AB154179, AB154181, AB154183, AB154185, AB154187, AB154189, AB154191, AB154193, AB154195, AB154197, AB154199, AB154201, AB154203, AB154205, AB191333, AB249644, AB429050, AF009606, AF139594, AF165045, AF165047, AF165049, AF165051, AF165053, AF165055, AF165057, AF165059, AF165061, AF165063, AF176573, AF207752-74, AF208024, AF313916, AF356827, AF483269, AF511948-50, AJ000009, AJ132996-97, AJ238799-800, AJ278830, AY045702, AY460204, AY587844, AY615798, AY695437, AY956463-8, D10749, D10934, D11168, D14484, D50480-82, D63857, D85516, D89815, D89872, D90208, DQ071885, DQ838739, EF032883, EF032886, EF032892, EF032900, EF407411-57, EF407458-504, EF621489, EF638081, EU155213-16, EU155217-35, EU155233, EU155236-381, EU234061, EU234063-65, EU239713, EU239714, EU239715-17, EU255927-99, EU255960-2, EU256000-1, EU256002-97, EU256045, EU256054, EU256059, EU256061-2, EU256064-6, EU256075-103, EU256104, EU256106-7, EU260395-6, EU362882, EU362888-901, EU362911, EU482831-2, EU482833, EU482834-89, EU482839, EU482849, EU482859, EU482860, EU482874, EU482875, EU482877, EU482879-81, EU482883, EU482885-6, EU482888, EU529676-81, EU529682, EU569722-23, EU595697-99, EU660383-85, EU660386, EU660387, EU660388, EU677248, EU677253, EU687193-95, EU857431, EU862823-24, EU862826-27, EU862835, FJ024086, FJ024087, FJ024274-76, FJ024277, FJ024278, FJ024279, FJ024280-82, FJ181999-201, FJ205867-69, FJ390394-95, FJ390396-8, FJ390399, FJ410172, L02836, M58335, M84754, U01214, U16362, U45476, U89019, X61596).

Hereinafter, the 390 subtype 1a sequence dataset is referred to as the "original dataset" for purposes of describing the present invention. The sequences were aligned using MUSCLEv3.0 (Nucleic Acids Res. 32:1792-1797 (2004)) and modified using BioEditv7.0.5.3108 (mbio.ncsu.edu/RNaseP/info/programs/BIOEDIT/bioedit.html (accessed 20 Feb. 2005)). To avoid idiosyncrasies of any individual phylogeny, we constructed 2 independent phylogenetic trees using a software program which allows phylogenetic reconstruction and ancestral sequence reconstruction as a probability distribution, e.g. MrBayesv3.2 (Bioinformatics 19:1572-1574 (2003)) applied to positions 869-1292 (Core/E1) and 8276-8615 (NS5B) from the full-genome alignment (position numbers are based on reference genome H77; Genbank accession number AF009606). These segments were chosen because they were shown to be most phylogenetically informative. They are hereinafter referred to as "Simmonds" regions in the present invention. 30 million iterations of MrBayesv3.2 were run and confirmed convergence of parameters for phylogenetic trees inferred from both Simmonds regions using Tracerv1.5 (Rambaut A, available from the author, [beast.bio.ed.ac.uk/Tracer]). Both Simmonds regions yielded different trees which is expected due to the large number of possible trees; nonetheless, analysis of these two dataset converged with similar model parameters. In addition, recombination in HCV is rare. Hence, it can be assumed that the same phylogenetic tree or same evolutionary history will be correct for the entire length of the genome.

Using both phylogenetic trees reconstructed with Simmonds regions, ancestral sequences were inferred for each of the HCV-1a coding regions. The ancestral sequence is obtained as a probability distribution for each position, such that there is a probability of observing each base.

Computational preparation of synthetic HCV genome. Bole1a was derived using an embodiment of the methods of the present invention.

1. For each nucleotide position i in the genome, if both trees agreed on the maximum posterior probability (MPP) residue, the probability of that position $p_i$ was selected to be the greater of the two MPPs. These positions are defined as concordant.

2. For discordant positions (where the MPP residue did not agree), the joint probability of the codon k containing the discordant position based on both trees was designated $pc_k$(core-E1) and $pc_k$(NS5B). For concordant residues within such codons, the $p_i$ calculated in the previous step was used in calculating the joint probability.

3. The codon with the higher joint MPP from the two trees was selected to represent that codon position. This codon-based analysis resolves cases where more than one position in the codon is discordant and accommodates 6-fold degenerate codons.

4. To determine a stringent threshold for codon MPP, the inflection in the distribution of codon MPPs at which the variance in second derivative was less than $10^{-6}$ for MPP values was found to be 0.9837, corresponding to individual residue MPPs>0.99.

5. Each codon with an MPP greater than or equal to 0.9837 based on either tree was accepted as ancestral and its constituent positions were defined as resolved.

6. Covariance analysis was used to examine still-unresolved positions. The basic assumption of phylogenetic reconstruction that each site evolves independently ignores covarying and interacting sites. In order to take such sites into consideration, the observed and expected frequencies of pairs of bases was determined and the chi-squared metric was calculated as shown in equation 1 and adjusted for multiple comparisons using the Holm-Bonferroni method at α=0.05.

$$\chi_{ij}^2 = (o_{ij} - e_{ij})/e_{ij} \qquad (1)$$

Using the adjusted chi-squared metric, all resolved positions j that significantly covaried with unresolved positions i were identified. In case of a positive interaction ($o_{ij} > e_{ij}$), the MPP codon containing the positively interacting residue was selected. For negative interactions ($o_{ij} < e_{ij}$), all codons with the negatively interacting base were eliminated and the MPP codon from the remaining is selected.

7. At still-unresolved sites, the MPP codon was selected even if less than 0.9837 (as noted in Example x, this was rarely necessary).

5' and 3' UTR sequence reconstruction. Although 5'UTR and 3'UTR are noncoding regions, they are essential in the replication of the virus. However, of the 390 sequences, only 6 had completely sequenced 5'UTR regions and 4 had completely sequenced 3'UTR regions. Hence we used additional sequences to better design the noncoding regions. The 5'-UTR (n=257) and 3'-UTR (n=46) sequences were from clonal sequences generated from acutely-infected subjects in the BBAASH cohort. We found that our 90% consensus sequence of the 5' UTR was identical to the consensus sequence derived from the 6 sequences with complete sequences and also to the H77 5'UTR. The 3'UTR sequence was divided into 4 parts based on classification by Kolykhalov et. al. We determined the 90% consensus sequence for the first part, which is a short sequence with significant variability among genotypes. For the second segment of the 3'UTR, we determined that the median length of the homopolymeric uracil tract was 51 residues, which is also a favorable length for replication. We selected a segment of median length for the third segment, a polypyrimidine tract consisting of mainly U with interspersed C residues. The last (3' end) part is a conserved sequence of 98 bases for which we used the 90% consensus sequence, was confirmed with 15 additional sequences from an unrelated study HCV pseudoparticle (HCVpp) system. A region of Bole1a nucleotide sequence encoding the last 27 amino acids of core followed by the E1 and E2 regions was synthesized (Blue Heron, Bothell, Wash.) and then subcloned into the expression vector pcDNA3.2/V5/Dest (Invitrogen, Carlsbad, Calif.) using Gateway cloning technology. The E1E2 region was sequenced after cloning and showed no errors. Pseudoparticles containing the luciferase reporter gene were generated as described (Proc. Natl. Acad. Sci. U.S.A 100: 7271-7276 (2003); Proc. Natl. Acad. Sci. U.S.A 101:10149-10154 (2004); Clininfect. Dis. 41:667-675 (2005)). Briefly, plasmid expressing Bole1a E1E2 was co-transfected into HEK293T cells with pNL4-3.Luc.R⁻E⁻ plasmid containing the env-defective HIV proviral genome and a luciferase reporter gene. The HCVpp containing supernatants were collected 48 and 72 hours after transfection. Pseudoparticles expressing E1E2 glycoproteins from H77, and from another subtype 1a HCV virus (pp1a46), as well as no E1E2 (mock) were produced in parallel with pseudoparticles expressing Bole1a E1E2 for comparison of infectivity. Serial two-fold dilutions of pseudoparticles were used to infect Hep3B hepatoma cells in duplicate wells of a 96-well plate for 5 hours, followed by replacement of media, and measurement of luciferase activity 72 hours post infection. Cells were lysed with Cell Culture Lysis Reagent (Promega, USA) and luciferase activity was measured using Luciferase Assay Reagent (Promega, USA) and a Centro LB960 Chemiluminometer (Berthold, Germany).

CD81 blocking experiments. Hep3b cells were incubated with a mouse anti-human CD81 monoclonal antibody (100 μg/ml, clone 1.3.3.22, Santa Cruz Biotechnology) or mouse IgG1 isotype control (Santa Cruz Biotechnology, USA) for 1 hr at 37° C., and HCVpp infection was assessed as above.

Neutralization by human plasma. Heat-inactivated plasma or serum was diluted 1:4 with MEM containing 10% FBS, incubated with each library HCVpp for 1 hour at 37° C. (final HCVpp dilution, 1:100), added to Hep3b hepatoma cells in duplicate wells of a 96-well plate and incubated for 5 hours at 37° C. followed by replacement of media. Luciferase activity was measured as above. HCVpp infection was measured in terms of relative light units (RLUs) in the presence of plasma or serum samples (RLUtest) versus average infection in the presence of normal human serum (Gemini Bio-Products, West Sacramento, Calif.) and plasma pooled from seronegative BBAASH participants (RLUcontrol). Percent neutralization was calculated as [1-(RLU test/RLUcontrol)]×100.

Figure 2A:
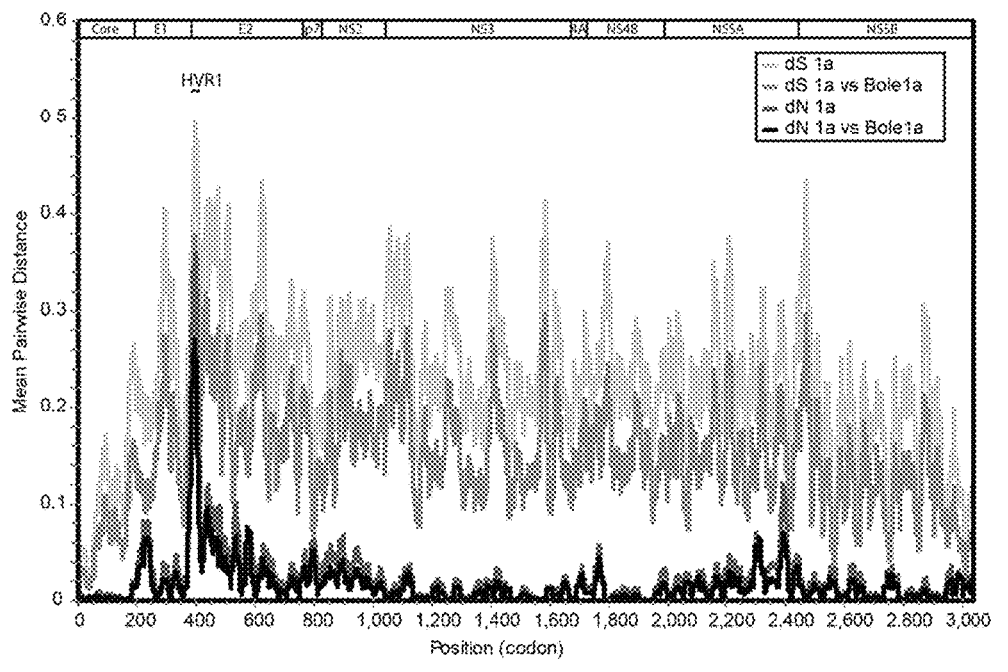
Figure 2B:
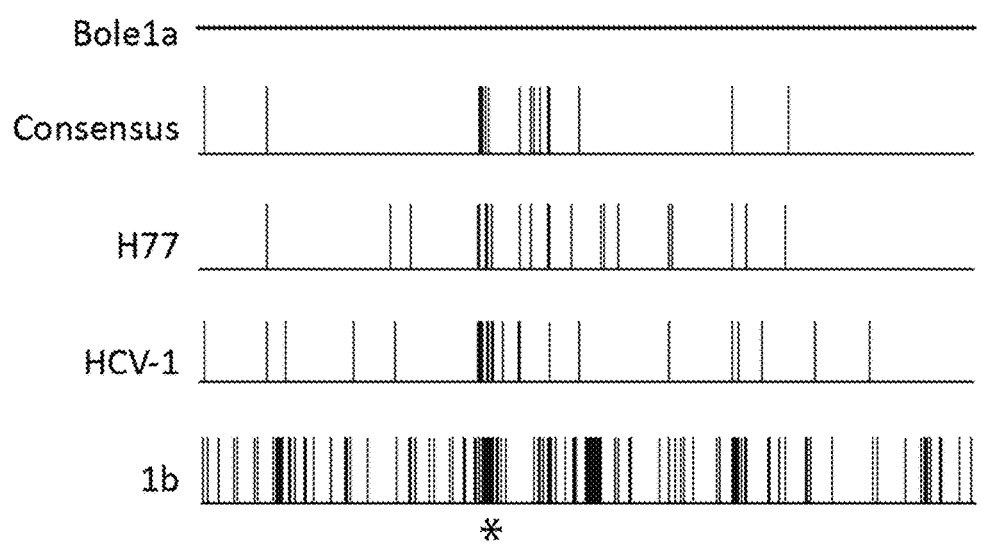
FIG. 2B shows an alignment comparison of E1E2 using Bole1a as the reference sequence and consensus (of 390 sequences), H77, HCV-1 and a 1b (D90208) sequence. Vertical bars indicate positions with amino acid differences in respective sequences compared to Bole1a and asterisk indicates the position of HVR1.
Figure 3A:
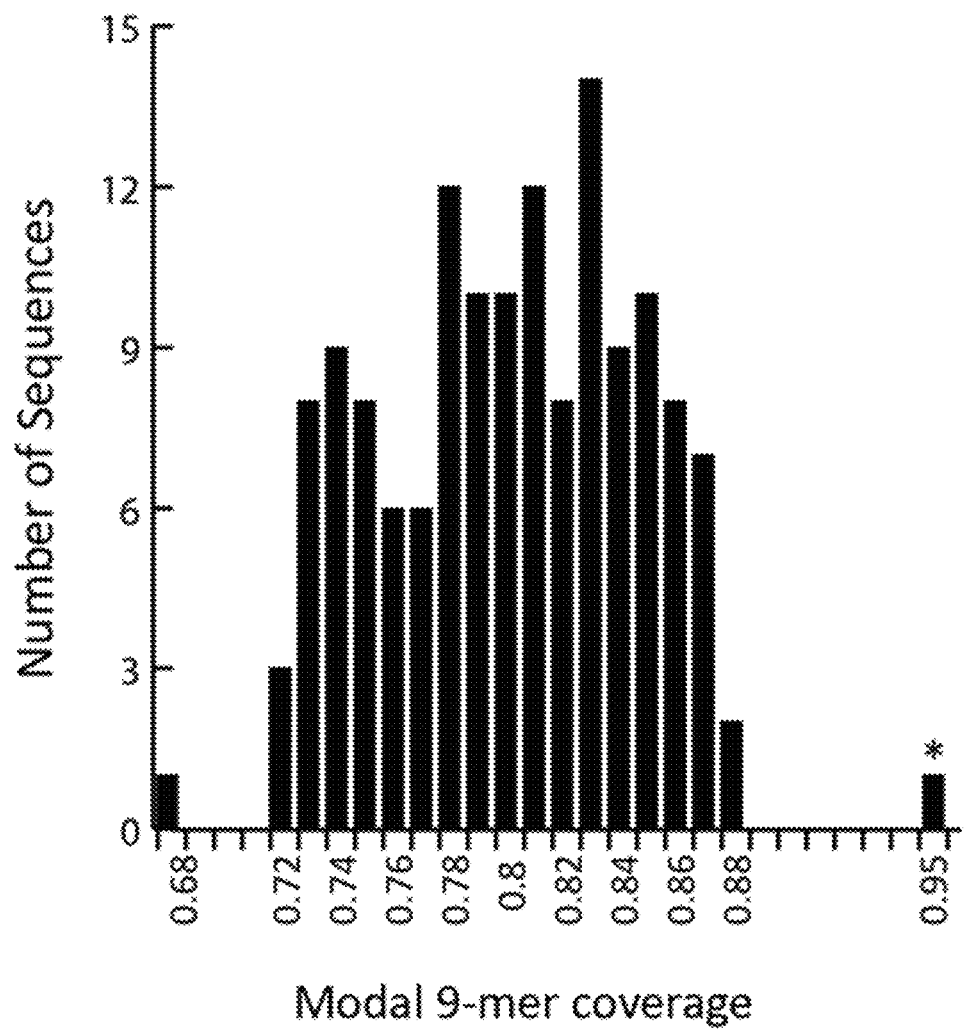
FIG. 3A depicts that Bole1a (indicated by asterisk) is highly representative based on (a) coverage of modal (most commonly-observed) 9-mers provided by Bole1a and all other sequences in the Yusim dataset.
Figure 3B:
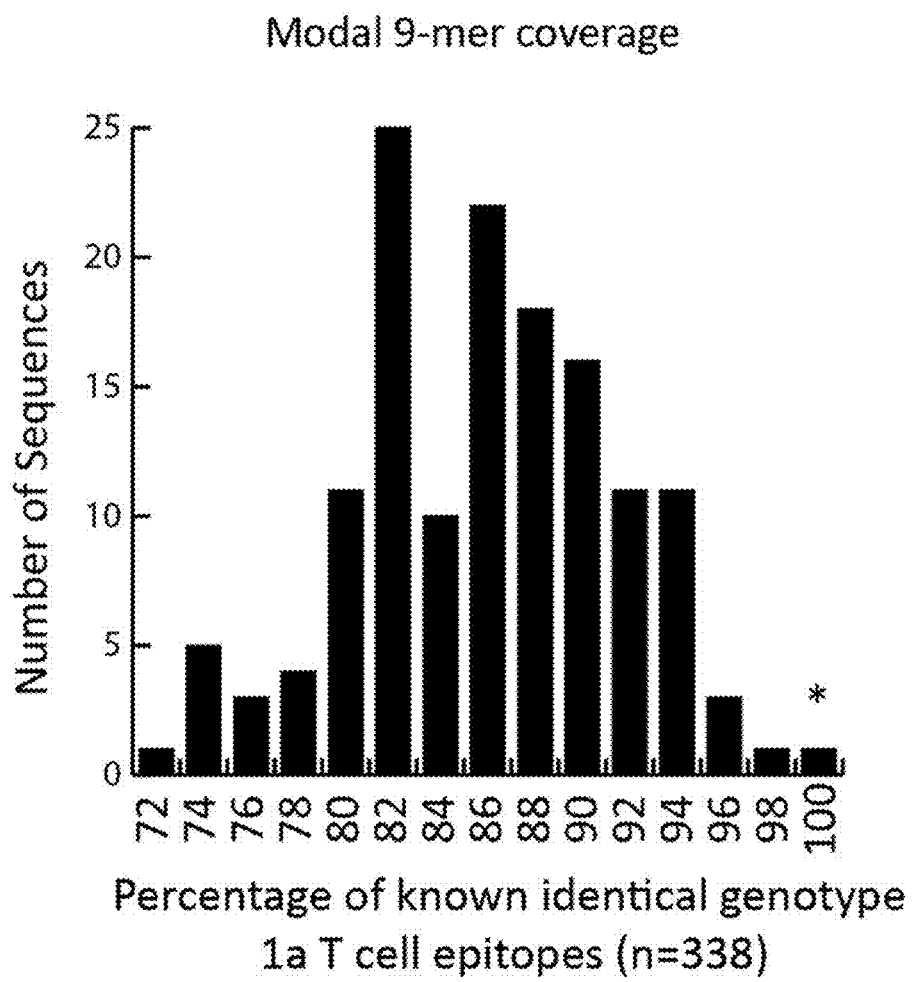
FIG. 3B shows identity to known epitopes, depicted as a histogram showing the percentage of epitope sequences that are identical sequences to the known and common 338 epitopes T cell epitopes.
Figure 4:
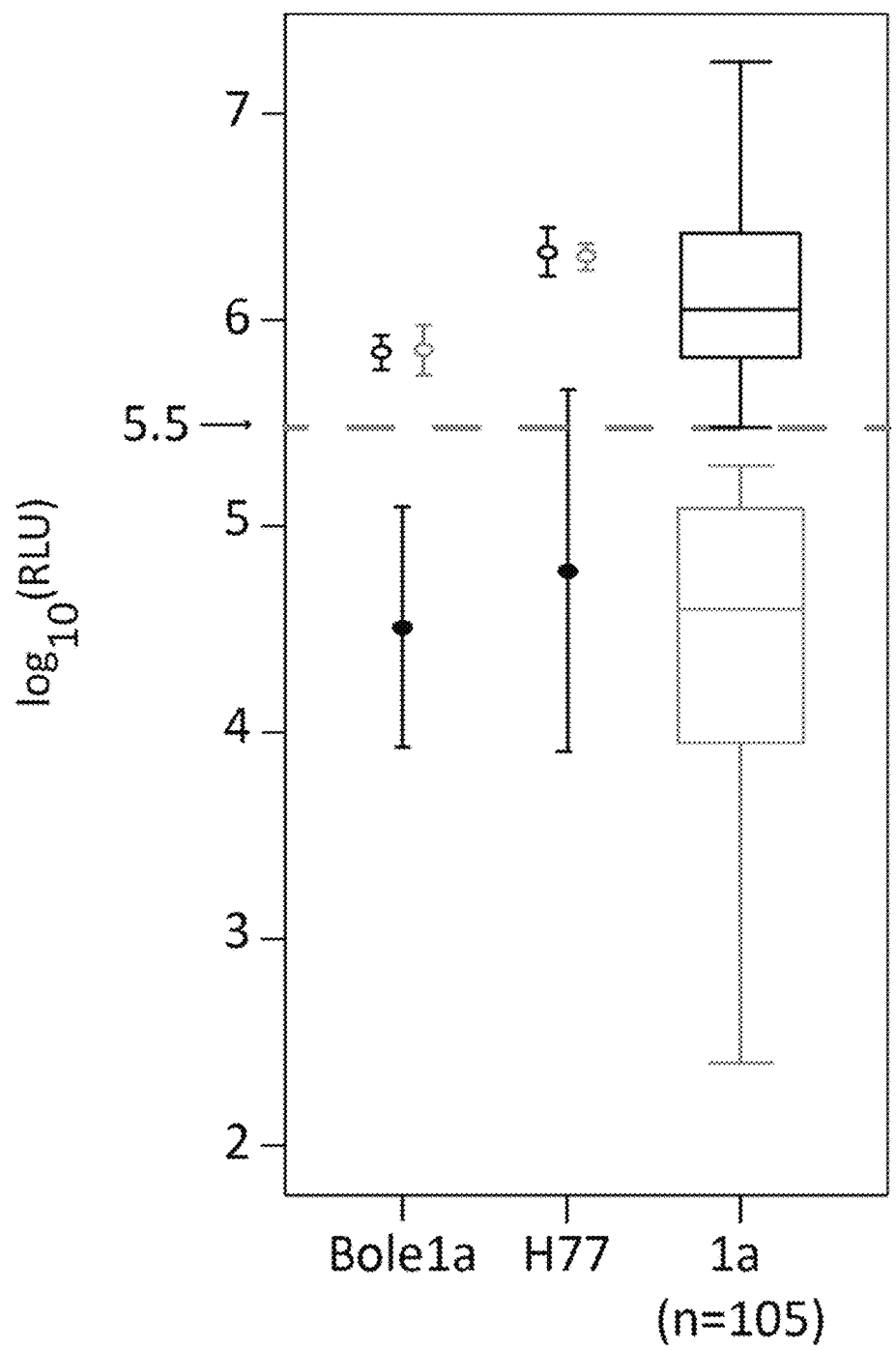
FIG. 4 shows the infectivity of various HCVpp is shown in log 10 (RLU). The black dotted line represents the RLU threshold for infectious HCVpp. The leftmost group of bars depicts the average infectivities of Bole1a with media only, Bole1a with anti-CD81, and Bole1a with an isotype control respectively. The middle group of bars depicts the average infectivities of H77 with media only, H77 with anti-CD81, and H77 with an isotype control respectively. Error bars are standard deviations calculated from 3 experiments. The two bars on the right show the average infectivities of all subtype 1a HCVpp that are infective (solid frame) and non-infective (dashed frame). The error bars represent standard deviation of infectivities.

Diversity analysis. Diversity plots were generated using VarPlot version 1.2 (available from the author at sray.med-.som.jhmi.edu/scroftware/VarPlot). Plots were generated using a window size of 20 codons (to reflect the upper limit of T cell epitopes) and a step size of 1. Nonsynonymous and synonymous distances were calculated using the models of Nei and Gojobori (Mol. Biol. Evol. 3:418-426 (1986)). The E1E2 pixel alignment (FIG. 2b) was drawn using VisSPAv1.6 (sray.med.som.jhmi.edu/SCRoftware/VisSPA/).

The Bole1a genomic sequence has been deposited in Genbank under accession # JQ791196.

Example 1

Trees for the E1 and NS5B regions generated ancestral sequences that agreed at 9763 (~98%) of 9992 nucleotide sites in the alignment (gaps were counted as characters). Applying the codon threshold of MPP of 0.9837 or higher in either tree left 68/3012 (2.2%) unresolved codons. Of these 68, 42 were choices between synonymous codons and 26 were choices between non-synonymous codons. Covariance networks were used to resolve ambiguities.

Example 2

Covarying positions. Of the 68 unresolved codons, 4 were determined based on dependence with resolved positions in the genome (H77 positions 1157, 1611, 2120, and 6554). All four of the positions (1157, 1611, 2120, and 6554) led to synonymous changes. Positions 1611 and 6554 were linked to multiple sites across the genome (50 and 3 respectively) whereas positions 1157 and 2120 were linked to one other resolved position. Because the covariance was only detected statistically, biological interaction is a question for further research.

Example 3

Figure 1B:
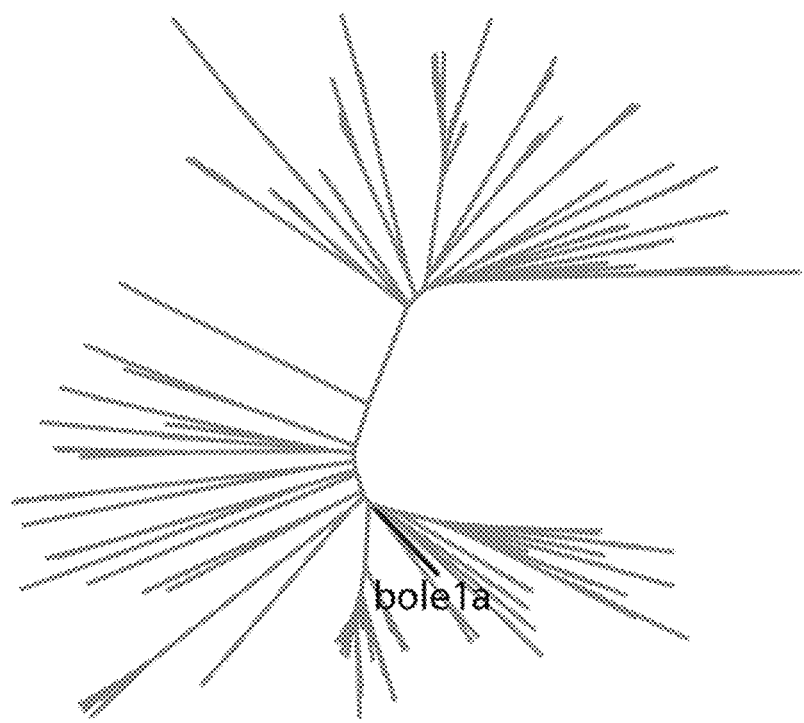

Representative characteristics of Bole1a. Once a complete representative sequence for Bole1a was determined, it was desired that to ensure that Bole1a represents any set of nucleotide or protein HCV subtype 1a sequences and not just the sequences from which it was reconstructed. In order to confirm this, two additional datasets were used for confirmation. The first dataset was from a paper by Yusim et al. (J. Gen. Virol. 91:1194-1206 (2010)) and collected from the Los Alamos HCV database. This dataset contains 143 sequences, 136 of which are present in the original dataset; however, the authors of that report curated the dataset to avoid resampling linked sequences. This dataset is referred to as the Yusim dataset. The second dataset, which is referred to as the E1E2 dataset, contains 214 E1E2 sequences; these were obtained from our ongoing BBAASH cohort. The sequences in the latter dataset are unrelated to any full-length sequences in GenBank or from the LANL database. Neighbor joining trees showed that Bole1a consistently branches from the center, suggesting that it is representative of both the Yusim and E1E2 datasets (FIG. 1).

Based on full-genome pairwise comparison, Bole1a has greater similarity to subtype 1a sequences than any other sequence in the original dataset (average and median reduction in non-synonymous distance of 39% and 44%, respectively, FIG. 2*a*). In sliding windows of 20 codons (approximating the upper limit on the size of T cell epitopes) spanning the genome, the similarity of Bole1a was greater than 98% overall (mean and median similarity 98.4% and 98.9%, respectively). Not surprisingly, the lowest similarity between Bole1a and subtype 1a circulating genomes was in hypervariable region 1 (HVR1), where similarity was as low as 73% (similarity among subtype 1a isolates at the same position was 64%). Comparison of Bole1a sequence to the consensus sequence of the original dataset, H77, HCV-1 and a 1b sequence demonstrates the high variability in HVR-1 (as shown by an asterisk, FIG. 2*b*).

All 9-mers of the Bole1a amino acid sequence were compared to sequences in the Yusim dataset to represent potential epitope coverage. The use of 9-mers for this comparison is based on the typical MHC class I-restricted epitope length recognized by effector CD8+ T cells that are a crucial component of immune control in spontaneous clearance of HCV infection. Bole1a provides 78% exact-match 9-mer coverage for the HCV polyprotein whether compared to the Yusim dataset or the original dataset (data not shown, method previously described in Yusim). In the highly-diverse E1 and E2 regions of the E1E2 dataset, Bole1a provides 58% exact-match 9-mer coverage. The Yusim dataset was then compared by individual proteins and confirmed that highly heterogeneous regions such as E1 and E2 have lower coverage by Bole1a than more conserved regions such as core and NS4B. In all cases, Bole1a provided greater 9-mer coverage than the reference sequence H77. Bole1a matched 99% of all 9-mers on full genome comparison when a mismatch at 1 or 2 positions was allowed. In summary, it was found that Bole1a matched 95% of all modal (most frequently-observed) 9-mers at each position of the genome whereas individual sequences in the Yusim dataset had a median modal 9-mer coverage of 80% (FIG. 3*a*).

Example 4

The obvious limitation of comparing 9-mer coverage is that not all 9-mers are recognized as T cell epitopes. To focus on epitope coverage all known subtype 1a T cell epitopes (both CD4 and CD8) were selected from the Immune Epitope Database (www.immuneepitope.org/) associated with a positive result in at least one assay. Of the 548 epitopes in the database, only 338 were present in at least half of the sequences of the Yusim dataset (excluding AF271632 and AX100563 due to their linkage with HCV-1 and H77, respectively). Bole1a had the highest (100%) coverage of these 338 epitopes (FIG. 3*b*). HCV-1 and H77, which are commonly used as antigens in HCV immunology, only matched 317 and 316 (~93%) of these 338 epitopes respectively. FIG. 3*b* shows the distribution of epitope coverage for all sequences in the Yusim dataset. When epitopes that were present in 80% of the sequences were included, Bole1a provided 94% coverage while H77 and HCV-1 provided 87% and 91% coverage respectively (data not shown). It should be noted that because HCV-1 and H77 have been the primary isolates used as antigens in many of the studies from which these epitopes are derived, their coverage may be due in part to analytical bias. Lastly, interferon gamma ELISpot analysis of variant epitopes demonstrated that variants in the Bole1a genome are more consistently immunogenic than other sequences, including H77 and a simple consensus (data not shown).

Example 5

Bole1a pseudoparticle. Approximately 75% of individual E1E2 isolates tested have low infectivity (less than 5 standard deviations above background) when used to pseudotype lentiviral particles (FIG. 4). The diversity of the envelope genes is extremely high with an average non-synonymous diversity of 36% in 20-codon windows (FIG. 2). As a result of this diversity and our methods, Bole1a has a unique HVR1 sequence (ETHVTGGSAARATAGFAGLFTPGAKQN) (SEQ ID NO: 3) among the genomes we have examined, and searches for this peptide sequence using BLAST (blast.ncbi.nlm.nih.gov) and HMMER (hmmer.janelia.org) did not reveal any identical sequences. To test functionality despite these negative predictors for infectivity, the E1E2 sequence of Bole1a was used to construct a lentiviral pseudoparticle. Surprisingly, HCVpp-Bole1a infected Hep3B target cells with high efficiency comparable to highly-infectious and well-characterized isolate HCVpp-H77 (FIG. 4). Blocking the Bole1a HCVpp with anti-CD81 antibody led to at least a 10 fold reduction in infectivity (p=0.0008) whereas the isotype control antibody did not change infectivity (p=0.85; FIG. 4). RLU values below the threshold (FIG. 4) are found to be reproducibly low with high variance. Although the comparison panel of subtype 1a HCVpp excluded those that contained stop codons, frameshift mutations, or other obvious defects, it is evident that there are other biological or artifactual characteristics that render many of those clones less infectious. Importantly, the goal of this experiment was to determine whether Bole1a E1E2 would be functional at all in spite of its synthetic origin and the high variability of HCV envelope; that this E1E2 was infectious in the HCVpp system was highly unexpected. Additionally, the Bole1a HCVpp was readily neutralized by human sera. It was observed that 30% of BBAASH subjects inhibited at least 85% of entry and 90% of subjects from the BBAASH cohort (36 out of 40) inhibited at least 50% of Bole1a HCVpp entry, whereas normal human serum and pooled HCV-seronegative sera were non-neutralizing.

This proof-of-concept study demonstrates that the Bole1a envelope E1E2 heterodimer is able to fold and assemble correctly. Because HCV E1 and E2 genes are critical for host cell entry, they are also important targets for antibody-mediated virus neutralization. Because it lacks evident immunologically-driven escape mutations, Bole1a may represent the ideal platform to study determinants of HCV fitness.

Example 6

Preliminary analyses have shown that epitopes from Bole1a are the most immunogenic of any isolate tested. In those cases where Bole1a epitopes differed from the traditional consensus (2 out of 15 tested), T cells from chronically infected patients recognized Bole1a epitopes better than the corresponding epitopes from circulating and consensus sequences (data not shown). Since Bole1a is representative of circulating strains, it is unlikely to contain escape mutations that hinder viral fitness. For example, the Bole1a sequence has a Y at position 1444 whereas an F at the position is believed to be an escape mutation causing the NS3 1436-1444 epitope to elicit a less robust T cell response. Additionally, Bole1a contains the KLVALGINAV (SEQ ID NO: 4) sequence at NS3 1406-1416. Three variants of this epitope have been shown to have diminished T cell response without a change in MHC binding ability making escape the most likely explanation for these variants.

Example 7

Using the above described methods of the present invention, two additional synthetic HCV genome polynucleotide sequences were prepared. The sequences are for a second HCV subtype 1a (SEQ ID NO: 5) and its resolved amino acid sequence (SEQ ID NO: 6), and HCV subtype 1b (SEQ ID NO: 7) and its resolved amino acid sequence (SEQ ID NO: 8).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. The polypeptide encoded by a nucleic acid comprising SEQ ID NO: 1, encoding the genome of the synthetic hepatitis C virus subtype 1a (Bole 1a).

2. The polypeptide of claim 1, comprising the amino acid sequence of SEQ ID NO: 2.

3. A viral particle comprising:
   a) the last 27 amino acids encoded by of the core sequence of SEQ ID NO: 1 followed by the amino acid sequences of the E1 and E2 regions; and
   b) a reporter element.

4. The viral particle of claim 3, wherein the reporter element comprises the luciferase polyprotein or a functional portion thereof.

* * * * *